(12) United States Patent
Reichlin et al.

(10) Patent No.: US 6,342,218 B1
(45) Date of Patent: *Jan. 29, 2002

(54) METHOD FOR TREATMENT OF SLE

(75) Inventors: Morris Reichlin, Oklahoma City, OK (US); Eugen Koren, San Francisco, CA (US)

(73) Assignee: Oklahoma Medical Research Foundation, Oklahoma City, OK (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/800,682

(22) Filed: Feb. 14, 1997

Related U.S. Application Data

(60) Provisional application No. 60/011,867, filed on Feb. 16, 1997.

(51) Int. Cl.$^7$ .................. A61K 39/395; A61K 39/385; C07K 38/00; C07K 16/42
(52) U.S. Cl. ........................ 424/131.1; 424/133.1; 424/192.1; 424/193.1; 514/12; 514/13; 514/14; 514/15; 514/16; 514/17; 514/18; 530/324; 530/325; 530/326; 530/327; 530/328; 530/329; 530/330; 530/387.1; 530/403
(58) Field of Search ........................ 424/131.1, 133.1, 424/192.1, 193.1; 514/12, 13, 14, 15, 16, 17, 18; 530/324, 325, 326, 327, 328, 329, 330, 387.2, 403

(56) References Cited

U.S. PATENT DOCUMENTS

| | | |
|---|---|---|
| 4,602,003 A | 7/1986 | Malinow |
| 4,944,944 A | 7/1990 | Tang et al. |
| 4,976,968 A | 12/1990 | Steiner |
| 5,017,565 A | 5/1991 | Lange, III et al. |
| 5,063,210 A | 11/1991 | Lange, III et al. |
| RE33,885 E | 4/1992 | Mattson |
| 5,173,408 A | 12/1992 | Lange, III et al. |
| 5,200,183 A | 4/1993 | Tang et al. |
| 5,376,640 A | 12/1994 | Miyazaki et al. |
| 5,519,001 A | 5/1996 | Kushwaha et al. |

FOREIGN PATENT DOCUMENTS

| | | |
|---|---|---|
| EP | 0 333 523 | 9/1989 |
| WO | WO 89/08465 | 9/1989 |
| WO | WO 91/06286 | 5/1991 |
| WO | WO 91/06287 | 5/1991 |
| WO | WO 91/15234 | 10/1991 |
| WO | WO 94/20610 | 9/1994 |

OTHER PUBLICATIONS

Aarden, et al., "Immunology Of DNA. III. Crithidia Luciliae, A Simple Substrate For The Determination Of Anti–dsDNA With The Immunofluo–Rescence Technique", *Ann. NY Acad. Sci.*, 254:505–515 (1975).

Altschul, et al., "Basic Local Alignment Search Tool", *J. Mol. Biol.*, 215:403–410 (1990).

Andre–Schwartz, et al., "Binding of Cytoskeletal Proteins By Monoclonal Anti–DNA Lupus Autoanti–Bodies", *Clin. Immunol., Immunopathol.*, 31:261 (1984).

Barada, et al., "Antibodies To Sm In Patients With Systemic Lupus Erythematosus", *Arthritis Rheum.*, 24:1236–1244 (1981).

Beaulieu, et al., "IgG Antibodies To Double–Stranded DNA In Systemic Lupus Erythematosus Sera", *Arthritis Rheum.*, 22:565–570 (1979).

Bloom, et al., "Overlap Of The Anti–Sm and Anti–DNA Responses Of MRL/MP–Ipr Mice", *J. Immunol.*, 150:1579 (1993).

Borel, et al., "Prevention Of Murine Lupus Nephritis By Carrier–Dependent Induction Of Immunologic Tolerance To Denatured DNA", *Science*, 182:76–77 (1973).

Borel, et al., "Treatment Of Lupus Nephritis In Adult (NZB+NZW)F Mice by Cortisone–Facilitated Tolerance To Nucleic Acid Antigens", *J. Clin. Invest.*, 61:276–286 (1978).

Borel & Borel, "Oligonucleotide Linked To Human Gammaglobulin Specifically Diminishes Anti–DNA Antibody Formation in Cultured Lymphoid Cells From Patients With Systemic Lupus Erythematosus", *J. Clin. Invest.*, 82:1901–1907 (1988).

Clackson, et al., "Making Antibody Fragments Using Phage Display Libraries", *Nature*, 352:624–688 (1991).

Clark, et al., "Characterization Of A Soluble Cytoplasmic Antigen Reactive With Sera From Patients With Systemic Erythmatosus", *J. Immunol.*, 102(1):117–122 (1969).

Dale, et al., "A Rapid Single–Stranded Cloning Strategy For Producing A Sequential Series Of Overlapping Clones For Use In DNA Sequencing: Application To Sequencing The Corn Mitochondrial 18S rDNA", *Plasmid*, 13:31–40 (1985).

Daugherty et al., "Polymerase Chain Reaction Facilitates The Cloning, CDR–Grafting, And Rapid Expression Of A Murinte Monoclonal Antibody Directed Against The CD18 Component Of Leukocyte Integrins", *Nucl. Acids Res.*, 19:2471–2476 (1991).

(List continued on next page.)

Primary Examiner—Christina Y. Chan
Assistant Examiner—F. Pierre VanderVegt
(74) Attorney, Agent, or Firm—Holland & Knight LLP

(57) ABSTRACT

Treatments have been developed for lupus patients using either anti-ID antibodies to dsDNA to block anti-dsDNA antibodies and/or kill the B cells producing the anti-dsDNA antibodies or ribosomal protein S1 peptides immunoreactive with anti-dsDNA antibodies. Examples demonstrate that (1) anti-dsDNA antibodies are cross-reactive with ribosomal protein S1, (2) anti-dsDNA antibodies suppress protein synthesis, presumably through inhibition of mRNA translation initiation, and (3) a normal human sera contains an anti-idiotypic antibody (anti-Id) to anti-dsDNA antibodies isolated from SLE patients which blocked the interactions between the anti-Id antibody fragment (Fab$_2$) and various anti-dsDNA preparations.

12 Claims, 7 Drawing Sheets

OTHER PUBLICATIONS

Devereux, et al., "C Comprehensive Set Of Sequence Analysis Programs For The VAX", *Nucleic Acids Res.,* 12:387–395 (1984).

DiValerio, et al., "Anti–DNA Antibodies Can React Specifically With DNA In The Context Of Glomeruli", *Clin. Res.,* 42:139A (1994).

Eklund, et al., "Cloning Of A cDNA Encoding A Human DNA–Binding Protein Similar To Ribosomal Protein S1", *Gene.,* 155:231–235 (1995).

Franzetti, et al., "Characterization And RNA–Binding Properties Of A Choloroplast S1–Like Ribosomal Protein", *J. Biol. Chem.,* 267:19075–19081 (1992).

Friguet, et al., "Measurement Of The True Affinity Constant In Solution Of Antigen–Antibody Complexes By Enzyme–Linked Immunosorbent Assay",*J. Immunol. Methods,* 77:305 (1985).

Gish & States, "Identification Of Protein Coding Regions By Database Similarity Search", *Nature Genetics,* 3:266–271 (1993).

Gonzalez & Rothfield, "Immunoglobulin Class And Pattern Of Nuclear Fluorescence In Systemic Lupus Erythematosus", *N. Engl. J. Med.,* 274:1333–1338 (1966).

Hamilton, et al., "Two Ro (SS–A) Autoantibody Responses In Systemic Lupus Erythematosus", *Arthritis Rheum.,* 31:496–505 (1988).

Handwerger, et al., "Palmerston North Mice Produce Antibodies To U1RNP And SM Particles", *Clin. Res.,* 42:315A (1994).

Hahn & Tsao, Antobodies To DNA: In Dubois, Systemic Lupus Erythematosus, Wallace & Hahn, Eds. Lea & Febiger, Philadelphia, PA, 195–201 (1993).

Harley, et al., "A Model For Disease Heterogeneity In Systemic Lupus Erythematosus: Relationship Between Histo–Compatibility Antigens, Autoantibodies, And Lymphopenia, Or Renal Disease", *Arthritis Rheum.,* 32(7):826–836 (1989).

Itoh, et al., "Heterogeneity Of The Ro–SSA Antigen An Autoanti–Ro/SSA Response: Evidence Of The Four Antigenically Distinct Forms", *Clin. Exp. Immunol.,* 81:45–51 (1990).

Jaco, et al., "Human Systemic Lupus Erythematosus Sera Contain Antibodies Against Cell Surface Protein(s) That Share(s) Eiptope(s) With DNA",*Proc. Natl. Acad. Sci. USA,* 83:6970 (1986).

Jaenisch, "Transgenic Animals," *Science,* 240:1468–1474 (1988).

Kabat, et al., Sequences Of Proteins Of Immunological Intereast, 4th Ed. (U.S. Dept. Health and Human Services, Bethesda, MD (1987).

Kasukawa & Sharp, Ed. (Excerpta Medica, Elsevier Science Pub., Amsterdam, 85–96 (1987) *Mixed Connective Tissue Disease And Anti–Nuclear Antibodies.*

Koffler, et al., "Antibodies To Polynucleotides In Human Sera: Antigenic Specificity And Relation To Disease", *J. Exp. Med.,* 134:294–312 (1971).

Koren, et al., "Murine and Human Antibodies to Native DNA that Cross–React with the A and D SnRNP Polypeptides Cause Direct Injury of Cultured Kidney Cells" *J. Immunol.,* 154(9):4857–4864 (1995).

Leoning, "The Frantionation of High–Molecular–Weight Ribonucleic Acid aby polyacrylamide–Gel Electrophoresis," *Biochem J.* 102:251 (1967).

Maddison, et al., "Patterns Of Clinical Disease Associated With Antibodies to Nuclear Ribonucleoprotein", *J. Rheumatol.,* 5:407–411 (1978).

Maddison & Reichlin, "Deposition Of Antibodies To A Soluble Cytoplasmic Antigen In The Kidneys Of Patients With Systemic Lupus Erthematosus", *Arthritis Rheum.,* 22:858–863 (1979).

Matter, et al., "Molecular Characterization of Ribonucleoprotein Antigens Bound by Antinuclear Antibodies," *Arthritis Rheum,* 25:1278 (1982).

Mattioli, et al., "Heterogeneity Of RNA Protein Antigens Reactive With Sera Of Patients With Systemic Lupus Erythematosus", *Arthritis Rheum.,* 17:421–429 (1974).

Mattioli, et al., "Characterization Of A Soluble Nuclear Ribonucleoprotein Antigen Reactive With Sle Sera", *J. Immunol.,* 107(5):1281–1290 (1971).

Miniter, et al., "Reassessment Of The Clinical Significance Of Native DNA Antibodies In Systemic Lupus Erythematosus", *Arthritis Rheum.,* 22(9):959–968 (1979).

Pennebaker, "Immunoglobulin Classes of DNA Binding Activity in Serum and Skin in Systemic Lupus Erythematosus," *Journal of Clinical Investigation,* 60:1331–1338 (1977).

Pisetsky, et al., "Specificity An Idiotypic Analysis Of A Monoclonal Anti–Sm Antibody With Anti–DNA Activity", *J. Immunol.,* 135:4080 (1985).

Poorman, et al., "Isolation and Characterization of Native Human Renin Derived From Chinese Hamster Ovary Cells," *Proteins: Structure, Function and Genetics,* 1(2):139–145 (1986).

Provost, et al., "Lupus Band Test in Untreated SLE Patients: Correlation of Immunoglobulin Deposition in the Skin of the Extensor Forearm with Clinical Renal Disease and Serological Abnormalities," *Journal of Investigative Dermatology,* 74(6):407–412 (1980).

Radic, et al., "Residues That Mediate DNA Binding Of Autoimmune Antibodies", *J. Immunol.,* 150:150:4966 (1993).

Raz, et al., "Anti–DNA Antibodies Bind Director To Renal Antigens An Induce Kidney Dysfunction In The Isolated Perfused Rat Kidney",*J. Immunol.,* 142:3076 (1989).

Raz, et al., "Cross–reactions of anti–DNA autoantibodies with cell surface proteins," *Eur. J. Immunol.,* 23:383–390 (1993).

Reichlin & Mattioli, "Correlation Of A Precipitin Reaction To An Rnaprotein Antigen And A Low Prevalence Of Nephritis In Patients With Systemic Lupus Erythematosus", *N. Engl. J. Med.,* 286:908–911 (1972).

Reichlin, et al., "Lupus Autoantibodies To Native DNA Cross–React With THe A And D SnRNP Polypeptides", *J. Clin. Invest.,* 93:443–449 (1994).

Reichlin, et al., "Characterization of Anti–dsDNA Antibodies: Cross Reaction with SnRNP Polypeptides and Cell–Binding Abilities" *The Immunologist,* 3/3, 84–88 (1995).

Sanger, et al., "DNA Sequencing With Chain Terminating Inhibitors", *Proc. Natl. Acad. Sci. USA,* 74:5463–5467 (1977).

Schnier & Faist, "Comparison Studies On The Structural Gene For The Ribosomal Protein S1 in Ten Bacterial Species", *Mol. Gen. Genet.,* 200:476–481 (1985).

Schnier, et al., "Cloning And Characterization Of A Gene From Rhizobium Melilotii 2011 Coding For Ribosomal Protein S1", *Nucleic Acids Res.,* 16:3075–3098 (1998).

Schur & Sandson, "Immunological Factors and Clinical Activity In Systemic Lupus Erythematosus", *N. Engl. J. Med.,* 278:533–538 (1982).

Sharp, et al., "Mixed Connective Tissue Disease–An Apparently Distinct Rheumatic Disease Syndrome Associated With A Specific Antibody To an Extractable Nuclear Antigen (ENA)", *Am. J. Med.,* 52:148–159 (1972).

Smith & Johnson, "Single–step Purification Of Polypeptides Expressed In *Escherichia Coli* As Fusions With Glutathions S–transferase", *Gene,* (Amst.), 67:31–(1988).

Subramanian, "Structure And Funcitons Of Ribosomal Protein S1", *Prog. Nucleic Acids Res. Mol. Biol.,* 28:101–142 (1983).

Talal, et al., "Immunologic Regulation of Spontaneous Antibodies to DNA and RNA; I. Significant of IgM and IgG Antibodies in SLE Patients and Asymptomatic Relatives," *Clin. exp. Immunol.,* 25:377–382 (1976).

Tan & Kinkel, "Characteristics Of A Soluble Nuclear Antigen Precipitatiing With Sera Of Patients With Systemic Lupus Erythematosus", *J. Immunol.,* 99(3):464–471 (1996).

Tan, et al., "Deoxyribonucleic Acid (DNA) And Antibodies To DNA In The Serum Of Patients With Systemic Lupus Erythematosus", *J. Clin Invest.,* 45:1732–1740 (1966).

Targoff, et al., "Anti–KJ: A New Antibody Associated with the Syndrome of Polymyositis and Interstitial Lung Disease," *J. Clin. Invest.,* 84:162.

Tsao, et al., "Structural Characteristics Of The Variable Regions Of Immunoglobulin Genes Encoding A Pathogenic Autoantibody In Murine Lupus", *J. Clin. Invest.,* 85:530–540 (1990).

Tsuzaka, et al., "Lupus Autoantibodies to Double–Stranded DNA Cross–React with Ribosomal Protein S1," *Journal of Immunology,* 156:1668–1675 (1996).

Vlahakos, et al., "Murine Monoclonal Anti–DNA Antibodies Penetrate Cells, Bind To Nuclei. And Induce Glomerular Proliferation And Proteinuria In Vivo[1],[2]" *J. Am. Soc. Nephrol.,* 2:1345–1354 (1992).

Wasicek & Reichlin, "Clinical And Serological Differences Between Systemic Lupus Erythematosus Patients With Antibodies To Ro Versus Patients With Antibodies To Ro and La", *J. Clin. Invest.,* 69:835–843 (1982).

Winfield, et al., "Specific Concentration Of Polynucleotide Immune Complexes In The Cryoprecipitates Of Patients With Systemic Lupus Erthematosus", *J. Clin. Invest.,* 56:563–570 (1975).

Winkler, et al., "IgG Human Monoclonal Anti–DNA Autoantibodies From Patients With Systemic Lupus Erythematosus", *Clin. Exp. Immunol.,* 85:379–385 (1991).

Yanase, et al., "A Subgroup Of Murine Monoclonal Anti–Deoxyribonucleic Acid Antibodies Of Murine Monoclonal Anti–Deoxyribonucleic Acid Antibodies Traverse The Cytoplasm And Enter The Nucleus In A Time–And Temperature–Dependent Manner", Lab. Invest., 71:52–60 (1994).

Young & Davis, "Efficient Isolation Of Genes By Using Antibody Probes", *Proc. Natl. Acad. Sci. USA,* 80:1194–1198 (1983).

Zack, et al., "DNA Mimics A Self–Protein That May Be A Target For Some Anti–DNA Antibodies In Systemic Lupus Erythematosus", *J. Immunol.,* 154:1987 (1995).

Sasaki, T et al. J. Clin. Invest. 77:1382–1386, Apr. 1986.

Hahn, B et al. J. Immunol. 132(1):187–190, Jan. 1984.

FIG. 2a

```
GGT GAA GAA GGA GTT GTG CCA GCA CGT GAG TAC TCA GAC GAT CGT   45
Gly Glu Glu Gly Val Val Pro Ala Arg Glu Tyr Ser Asp Asp Arg  [15]

AAC ATC AAC CTG GCA GAC GAA TTA AAA ATT GGT GAT ACC ATT GAA   90
Asn Ile Asn Leu Ala Asp Glu Leu Lys Ile Gly Asp Thr Ile Glu  [30]

GCA GTT GTC ATT TCT AAC GTA ACA AGC GAC AAG GAA GGC GTC AGT  135
Ala Val Val Ile Ser Asn Val Thr Ser Asp Lys Glu Gly Val Ser  [45]

TAC TTG TTG TCA AAG AAG CGT TTG GAT GCG CGC AAG GCA TGG GAA  180
Tyr Leu Leu Ser Lys Lys Arg Leu Asp Ala Arg Lys Ala Trp Glu  [60]

AAC TTG AGC TTT GCT GAA GGT GAC ACA GTT GAT GCC AAG GTT ATC  225
Asn Leu Ser Phe Ala Glu Gly Asp Thr Val Asp Ala Lys Val Ile  [75]

AAC GCT GTT CGT GGT GGT TTG ATT GTT GAT GTT AAC GGC GTA CGT  270
Asn Ala Val Arg Gly Gly Leu Ile Val Asp Val Asn Gly Val Arg  [90]

GGT TTC GTA CCA GCA TCA ATG GTT GCA GAA CGT TTC GTT TCT GAT  315
Gly Phe Val Pro Ala Ser Met Val Ala Glu Arg Phe Val Ser Asp [105]

TTG AAC CAA TTC AAG AAT AAG GAT ATT AAA GCA CAA GTT ATC GAA  360
Leu Asn Gln Phe Lys Asn Lys Asp Ile Lys Ala Gln Val Ile Glu [120]

ATT GAC CCT GCT AAT GCA CGT TTG ATT TTG TCA CGT AAG GCT GTT  405
Ile Asp Pro Ala Asn Ala Arg Leu Ile Leu Ser Arg Lys Ala Val [135]

GCT GCA CAA GAA CGC GCT GCA CGA TTG GCT GAA GTA TTT AGC AAG  450
Ala Ala Gln Glu Arg Ala Ala Gln Leu Ala Glu Val Phe Ser Lys [150]

TTG TCA GTT CGT GAA GTT GTT GAA GGA ACT GTT GCC CGT TTG ACA  495
Leu Ser Val Arg Glu Val Val Glu Gly Thr Val Ala Arg Leu Thr [165]

GAC TTC GGC GCA TTC GTT GAC TTG GGT GGT GTT GAT GGT TTG GTT  540
Asp Phe Gly Ala Phe Val Asp Leu Gly Gly Val Asp Gly Leu Val [180]

CAC GTA TCA GAA ATC TCA CAC GAT CGT GTG AAG AAC CCG GCC GAT  585
His Val Ser Glu Ile Ser His Asp Arg Val Lys Asn Pro Ala Asp [195]

GTA TTG ACA AAG GGT GAC AAG GTT GAT GTT AAG ATC TTG GCA TTG  630
Val Leu Thr Lys Gly Asp Lys Val Asp Val Lys Ile Leu Ala Leu [210]

GAC ACT GAA AAG GGT CGT ATC TCA TTG TCA ATC AAA GCA ACA CAA  675
Asp Thr Glu Lys Gly Arg Ile Ser Leu Ser Ile Lys Ala Thr Gln [225]
```

FIG. 2b

| | | | | | | | | | | | | | |
|---|---|---|---|---|---|---|---|---|---|---|---|---|---|
| CGT | GGA | CCT | TGG | GAC | GAA | GCT | GCA | GAT | CAA | ATC | GCT | GCA | GGT | TCA | 720 |
| Arg | Gly | Pro | Trp | Asp | Glu | Ala | Ala | Asp | Gln | Ile | Ala | Ala | Gly | Ser | [240] |

```
CGT GGA CCT TGG GAC GAA GCT GCA GAT CAA ATC GCT GCA GGT TCA   720
Arg Gly Pro Trp Asp Glu Ala Ala Asp Gln Ile Ala Ala Gly Ser  [240]

GTG CTT GAA GGT ACT GTT AAG CGT GTG AAG GAC TTT GGT GCC TTT   765
Val Leu Glu Gly Thr Val Lys Arg Val Lys Asp Phe Gly Ala Phe  [255]

GTT GAA ATT TTG CCT GGT ATC GAA GGT CTT GTG CAC GTG TCA CAA   810
Val Glu Ile Leu Pro Gly Ile Glu Gly Leu Val His Val Ser Gln  [270]

ATT TCA AAC AAG CGT ATT GAA AAC CCA TCA GAA GTT TTG AAG TCT   855
Ile Ser Asn Lys Arg Ile Glu Asn Pro Ser Glu Val Leu Lys Ser  [285]

GGT GAC AAG GTA CAA GTG AAG GTA TTG GAC ATT AAG CCA GCC GAA   900
Gly Asp Lys Val Gln Val Lys Val Leu Asp Ile Lys Pro Ala Glu  [300]

GAA CGT ATT TCA TTG TCA ATG AAG GCT TTG GAA GAA AAG CCA GAA   945
Glu Arg Ile Ser Leu Ser Met Lys Ala Leu Glu Glu Lys Pro Glu  [315]

CGT GAA GAT CGT CGT GGT AAC GAT GGT TCA GCT TCA CGT GCT GAT   990
Arg Glu Asp Arg Arg Gly Asn Asp Gly Ser Ala Ser Arg Ala Asp  [330]

ATC GCT GCT TAC AAG CAA CAA GAT GAC TCA GCC GCA ACA TTG GGT  1035
Ile Ala Ala Tyr Lys Gln Gln Asp Asp Ser Ala Ala Thr Leu Gly  [345]

GAC ATC TTT GGT GAT AAG TTG TAA GAGGCATCAACATAAAAGAGCTGGTTC  1086
Asp Ile Phe Gly Asp Lys Leu ***                              [352]

GCCAGTTCTTTTATTTTTGAAGAAAAATTGAGTGGGCATTAGTGGGCGCTCACGGTATG  1145

AAAAAGGAGGTGCGATTATGGCAGCACCAGTAGTAGCCATTGTTGGCGACCAAACGTCG  1204

GAAAATCGACTATCTTTAACCGGATGGCCGGAGAACGTATTGCAATTGTTGAAGATCAA  1263

CCAGGGGTAACACGCGATCGTTTGTACGCGCCAGCCGAATGGTTGAATTAT          1314
```

FIG. 3a

```
HS1  63 SFAEGDTVDAKVINAVRGGLIVDVNGVRGFVPASMVAERFVSDLNQFKNKDIKAQVIEI 121
ES1 101 AYEDAE--TGVINGK-K---FT-ELD-I-A-L-G-L- DV-P-R-TLHLEG-ELEFK--KL 159
RS1 107 K-EA-ER-EGI IF-Q-K---FT--LD-AVA-L-R-Q-DI-PIR-VTPADAQPAALRNLKM 165
PS1   1     E--TGVINGK-K---FT-EL--I-A-L-G-L- DV-P-R-TTHLEG -ELEFK--KL  54
CS1 182   --DVV-KG--IVG-NK--VVAL-E-L-----F-QISSK -SAEELLE -E-PLKFV -V 236
                                          a             b         c
                                         ****       ******      ***

HS1 122 DPANARLILSRKAVAAQERAAQLAEVFSKLSVGEVVEGTVARLTDFGAFVDLGGVDGLV 180
ES1 160 -QKRNNVVV--R--IES-NS-ERDQLLEN-QE-ME-K-I-KN---Y------------L 218
RS1 166 -KRRGNIW--RT-LEES--E-RS-IVQN-EE-Q----V-KNI--Y------------L 224
PS1  55 -QKRNNVVV--R--IES-SS-ERDQLLEN-QE-ME-K-I-KN---Y------------L 113
CS1 237 -EEQS--VM-NRKAM-DSQ- M-DSQAQ-GI-S---T---QS-KPY--I--I---IN--L 287
                              d                    e
                             ****                *****

HS1 181 HVSEISHDRVKNPADVLTKGDKVDVKILALDTEKGRISLSIKATQRGPWDEAADQIAAG 239
ES1 219 -ITDMAWK---H-SEIVNV--EIT--V-KF-R-RT-V--GL-QLGED--VAI-KRYPE- 277
RS1 225 --TDMAWR--H-SEIQNI -QQ-K-Q-IRINQ-TH----GM-QLESD---GIGAKYPV- 283
PS1 114 -ITDMAWK---H-SEIVNV--EIT--V-KF-R-RT-V--GL-QLGED--VAI-KRYPE- 172
CS1 288 ----Q-----SDI-T-QP--TLK-M-SH-R-R--V---T-KLEPT-G-              337
               a         b                  c                 d
              ****     ******             *******           ****
```

FIG. 3b

```
HS1 240 SVLEGTVKRVKDFGAFVEILPGIEGLVHVSQISNKRIENPSEVLKSGDKVQVKVLDIKP    298
ES1 278 TK-IT-R-TNLT-Y-C----EE-V-------EM RD-V-DATL--SV--E-EA-FTGVDR  510
RS1 284 KKIS----TNIT-Y-----LE------I-I-EM -RPG-QVI-EFNK---V-RAV---VDV  430
PS1 173 TK-T-R-TNLT-Y-C----EE-V-------EM          -K---E IAAV--QVDA  319
                            e
                         *****

HS1 299 AEERISLSMKALEEKPERE 317
ES1 511 KNRA-----VR-KD-AD-KD 529
RS1 431 DK------GI-QL         442
PS1 320 ER------GV-QLA-DP    335
```

METHOD FOR TREATMENT OF SLE

This application claims priority to International Application No. PCT/US96/07597 filed May 24, 1996 and Provisional patent application U.S. Serial No. 60/011,867 filed Feb. 16, 1996.

The U.S. government has rights in this invention by virtue of National Institutes of Health grant No. AR31133, R01 AR32214, and P01 AI2156 to Morris Reichlin.

BACKGROUND OF THE INVENTION

The present invention includes methods and reagents for treatment of Systemic Lupus Erythematosus ("SLE") patients characterized double stranded (ds) DNA by administration of reagents reactive with doublestranded DNA antibodies to alleviate damage resulting from the antibodies.

Relationship of Antibodies to dsDNA, the RNAproteins Ro/SSA, La/SSB, $U_1$RNP, and Sm, and Clinical Disease Expression The laboratory directed by Morris Reichlin at the Oklahoma Medical Research Foundation, Oklahoma City, Okla., has been engaged in the study of autoimmune responses to RNAprotein antigens in SLE patients for over 20 years. Researchers have reported the initial descriptions of the Ro/SSA (Clark, G. M., Reichlin, M. and Tomasi, T. B. *J. Immunol.*, 102:117–122 (1969)), La/SSB (Mattioli, M. and Reichlin, M. *Arthritis Rheum.*, 17:421–429 (1974)), and nRNP($U_1$RNP) (Mattioli, M. and Reichlin, M. *J. Immunol.*, 107:1281–1290 (1971)) systems, while others described the Sm antigen (Tan, E. M. and Kunkel, H. G. *J. Immunol.*, 99:464–471 (1966)).

Over time, it has become apparent that certain profiles of anti-RNA protein antibodies are positively correlated with nephritis while other profiles are "negatively" correlated or "protected" from the development of serious renal disease. Thus, antibodies to nRNP($U_1$RNP) alone were found to have a low frequency of nephritis (Sharp, G. C., et al. *Am. J. Med.*, 52:148–159 (1972); Reichlin, M. and Mattioli, M. *N. Engl. J. Med.*, 286:908–911 (1972)) while patients with both anti-nRNP and anti-Sm (or anti-Sm alone) had a high frequency of nephritis (Reichlin, M. and Mattioli, M. *N. Engl. J. Med.*, 286:908–911 (1972); Maddison, P. J., et al. *J. Rheumatol.*, 5:407–411 (1978)). In patients with anti-Ro/SSA alone, a high frequency of nephritis was noted (Wasicek, C. A. and Reichlin, M. *J. Clin. Invest.*, 69:835–843 (1982); Hamilton, R. G., et al., *Arthritis Rheum.*, 31:496–505 (1988); Harley, J. B., et al. *Arthritis Rheum.*, 32(7):826–836 (1989)), while in those with both anti-Ro/SSA and anti-La/SSB, a low prevalence of nephritis was found. Studies of acid eluates from lupus nephritis kidneys have demonstrated enrichment of anti-Ro/SSA compared to serum levels (Maddison, P. J. and Reichlin, M. *Arthritis Rheum.*, 22:858–863 (1979)), supporting the participation of Ro/SSA-anti-Ro/SSA complexes in the development and/or the perpetuation of the nephritis. Elution studies of antibodies to the $U_1$RNP/Sm complex also showed enrichment, but the precise specificities of these complexes (anti-Sm or anti-nRNP) were not determined because of technical limitations (Koffler, et al. *J. Exp. Med.*, 134:294–312 (1971)). Serum levels of anti-Sm antibodies have been shown to fluctuate with disease activity (including nephritis) in some SLE patients (Barada, et al., *Arthritis Rheum.*, 24:1236–1244 (1981)). These data indicate a role for the Ro/SSA and Sm systems in the development of nephritis, but only 50% of patients with either anti-Ro/SSA alone or anti-nRNP and anti-Sm (or anti-Sm alone) develop nephritis.

Much data support a major role for the DNA-anti-DNA system in the pathogenesis of lupus nephritis. Clinical studies show that high serum anti-DNA levels correlate positively with the activity of nephritis, and that remissions are associated with declining anti-DNA levels (Harley, et al., *Arthritis Rheum.* (1989); Tan, et al. *J. Clin Invest.*, 45:1732–1740 (1966); Schur, P. H. and Sandson, J. *N. Engl. J. Med.*, 278:533–538 (1982)). Anti-DNA has been shown to be enriched in serum cryoglobulins (Winfield, et al., *J. Clin. Invest.*, 56:563–570 (1975)) and in acid eluates of lupus nephritis kidneys (Maddison and Reichlin (1979); Miniter, et al., *Arthritis Rheum.*, 22:959–968 (1979); Beaulieu, et al. *Arthritis Rheum.*, 22:565–570 (1979)). In all these studies, the specificity of these antibodies are to dsDNA (double stranded or native DNA).

Antibodies to native or ds DNA play a special role in the clinical diagnosis and pathology of Systemic Lupus Erythematosus (SLE). These autoantibodies are highly specific, frequently correlate positively with disease activity (especially nephritis), and remissions are usually associated with declining anti-dsDNA levels (Hahn and Tsao, Antibodies to DNA. -Tn Dubois, Systemic Lupus Erythematosus. D-J. Wallace and B. H. Hahn, editors. (Lea and Febiger, Philadelphia, Pa. 1993) pp. 195–201; Harley, et al., *Arthritis Rheum.* 32:826–836 (1989); Tan, et al., *J. Clin. Invest.* 45:1732–1740 (1966); Schur and Sandson, *N. Engl. T. Med.* 278:533–538 (1982)). Patients who produce antibodies to the Ro/SSA and La/SSB (Harley, et al. (1989); Wasicek and Reichlin, *J. Clin. Invest.* 69:835–843 (1982); Hamilton, et al., *Arthritis Rheum.* 31:496–505 (1988); antigens as well as those that only have precipitins to $U_1$RNP (Sharp, *Am. J. Med.* 52:148–159 (1972); Reichlin and Mattioli, *N. Engl. J. Med.* 86:908–911 (1972)) very infrequently have anti-dsDNA in their serum and have a correspondingly low prevalence of nephritis. The mechanisms of these negative relationships of antibodies to Ro/SSA and La/SSB and $U_1$RNP with anti-dsDNA are not understood.

Studies have been reported in the literature describing differences in the ability of murine monoclonal antibodies to dsDNA to induce nephritis when hybridomas producing these antibodies are placed in normal mice (Tsao, et al. *J. Clin. Invest.*, 85:530–540 (1990)). Others have shown that murine monoclonal antibodies penetrate cells, bind to nuclei, and induce glomerular proliferation and proteinuria in vivo (Vlahakos, et al., *J. Am. Soc. Nephrol.* 2:1345–1354 (1992)). Most recently, others have reported direct in vitro binding of murine monoclonal antibodies to glomeruli which is DNA dependent (DiValerio, et al., *Clin. Res.*, 42:139A (1994)).

Reichlin, et al., *The Immunologist* 3/3, 84–88 (1995), characterizes anti-dsDNA antibodies as cross-reactive with unfolded or denatured A and D SnRNP polypeptides. Koren, et al., *J. Immunol.* 154:4857–4864 (1995), reported that murine and human antibodies to native DNA that cross-react with the A and D SnRNP polypeptides cause direct injury of cultured kidney cells. However, many questions remain about the mechanisms of lupus nephritis and the role of antibodies to dsDNA.

It is therefore an object of the present invention to provide methods and reagents for neutralizing the pathogenicity of antibodies to double stranded (ds) DNA.

It is another object of the present invention to develop specific therapy based on anti-idiotypes to anti-dsDNA.

SUMMARY OF THE INVENTION

Treatments have been developed for lupus patients using either anti-ID antibodies to dsDNA to block anti-dsDNA antibodies and/or kill the B cells producing the anti-dsDNA antibodies or ribosomal protein S1 peptides immunoreactive with anti-dsDNA antibodies. Examples demonstrate that (1) anti-dsDNA antibodies are cross-reactive with ribosomal protein S1, (2) anti-dsDNA antibodies suppress protein synthesis, presumably through inhibition of mRNA translation initiation, and (3) a normal human sera contains an anti-idiotypic antibody (anti-Id) to anti-dsDNA antibodies isolated from SLE patients which blocked the interactions between the anti-Id antibody fragment ($Fab_2$) and various anti-dsDNA preparations.

BRIEF DESCRIPTION OF THE DRAWINGS

FIGS. 2 and 2a are the nucleotide (SEQ ID NO:1) and deduced amino acid (SEQ ID NO:2) sequences of the cDNA insert in G7. Asterisks show the stop codon. This sequence has been added to the GenBank nucleic acid sequence database, Los Alamos National Laboratory, N.Mex., and has been assigned accession number U27517.

FIG. 3 is an alignment of the central core regions of 5 ribosomal proteins (SEQ ID NOS:3 to 7) (r-proteins) S1. Asterisks show the 5 repeating regions (SEQ ID NOS:8 to 12) (a, b, c, d, and e, respectively). Spaces indicate positions where gaps were introduced to optimize alignment of the sequences (SEQ ID NOS:3 to 7). Dashes indicate identity to the residues of HS1 (SEQ ID NO:3). Alignment of the central core region of HS1 (SEQ ID NO:3) is residues 63–317. HS1; human r-protein S1 (SEQ ID NO:3) presented in this study, ES1; E. coli r-protein S1 (SEQ ID NO:4) (Ref. 26), RS1; Rhizobium melilotii r-protein S1 (SEQ ID NO:5) (Ref. 28), PS1, Providencia sp. r-protein S1 (SEQ ID NO:6) (Ref. 27), CS1; chloroplast r-protein S1 (SEQ ID NO:7) (Ref. 29).

DETAILED DESCRIPTION OF THE INVENTION

Therapeutic Applicants and Pharmaceutical Compositions

Figure 1:
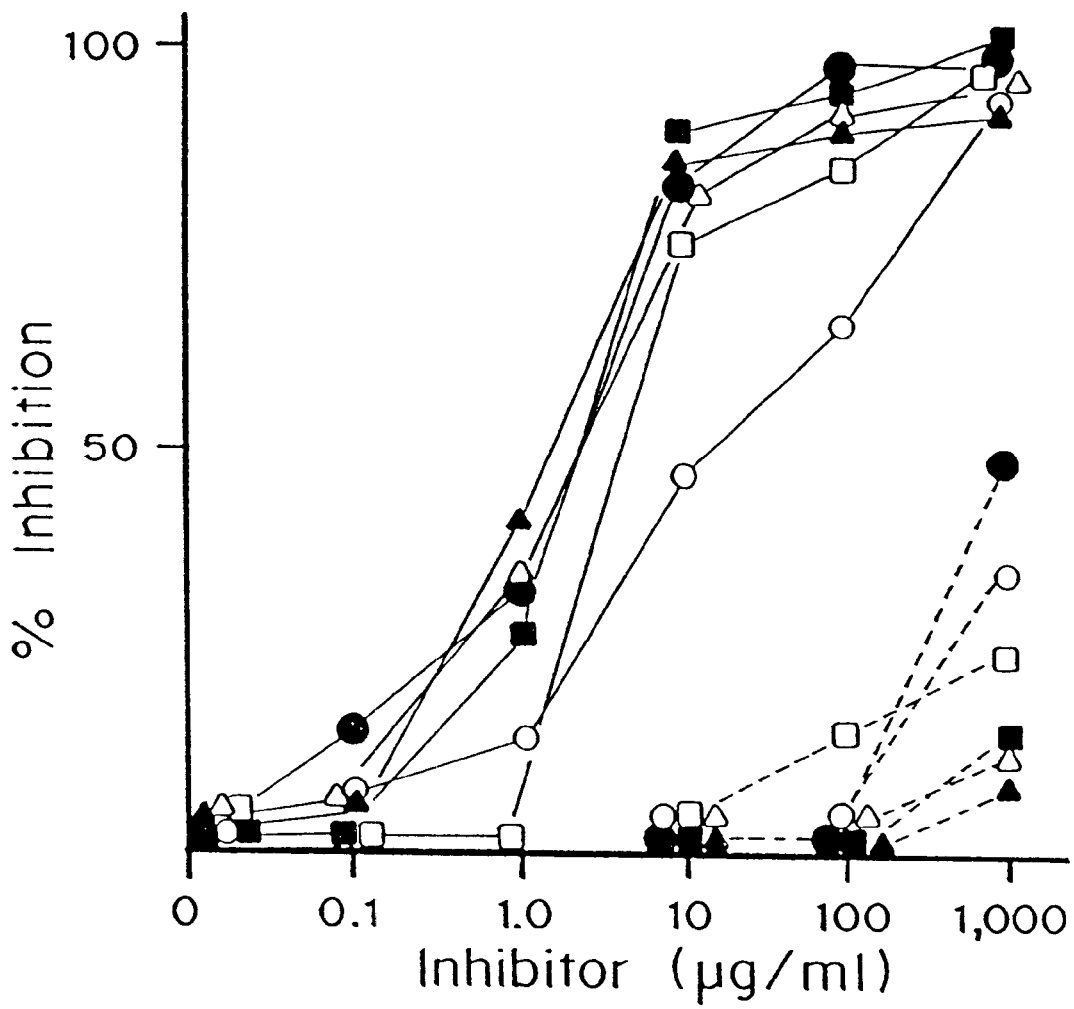
FIG. 1 is a graph of the inhibition of antibody binding to the recombinant protein (G7-RP) by DNA in ELISA. 5.0 µg/ml of G7-RP was used to coat the ELISA plates. 33.C9 (●), 33.H11(○), patient sera LG (▲) and JP (Δ), anti-dsDNA(AP) (■), and anti-dsDNA(IK) (□) were preincubated with 0, 0.1, 1.0, 10, 100, or 1,000 µg/ml of calf thymus dsDNA ( ----- ) in place thereof or Yeast tRNA ( - - - ) before being added to the plates.

Based on the results in the examples, one can prepare anti-Id reagents (for anti-dsDNA) that can be used to down-regulate the production of anti-dsDNA.

In one embodiment, reagents that are anti-idiotypic antibodies to anti-dsDNA could be used to down regulate or even curtail anti-dsDNA production by SLE patients.

In a second embodiment, free peptide or a conjugate of this peptide based on peptide sequence of human ribosomal protein S1 can be used in tolerance induction which could ablate anti-dsDNA.

Peptide or Protein-based Compositions

Attempts to influence anti-DNA production in mouse lupus in vivo or in human lymphocytes in vitro, are described by Borel, et al., Science, 182:76–77 (1973); Borel, et al., J. Clin. Invest., 61:276–286 (1978); Borel, Y. and Borel, H., J. Clin. Invest., 82:1901–1907 (1988). As described by Borel, et al., oligonucleotides or nucleosides are attached to isologous (same species) IgG and this is allegedly effective in (1) inhibiting the development of an immune response to DNA in murine lupus and decreasing disease severity, and (2) inhibiting human cells from producing anti-DNA in vitro. The "DNA" used by Borel is single stranded or denatured which is not optimal since the most important response in SLE is to native or double stranded DNA. Borel's work provides an appropriate "carrier" for the toleragen, isologous gamma globulin.

As described herein, peptide(s) that are immunoreactive with dsDNA and are derived from the human ribosomal protein S1 can be used to induce tolerance in a patient. Antibodies to dsDNA are the disease specific pathogenic autoantibodies of the greatest interest. There are two major possibilities: (1) inject free peptide, or (2) inject peptide-coupled to human IgG, for example, coupled using glutaraldehyde or carbodiimide. These two approaches should both induce T cell tolerance. They may also be effective in inducing B cell tolerance. Both approaches are attractive since there is little chance of "boosting" the anti-dsDNA response. Should the latter occur, it can be treated by standard immunosuppressive drugs, alone or in combination with anti-La/SSB or anti-$U_1$RNP, as described below.

Behavior of the peptide or peptide conjugate is first studied in an appropriate animal model in order to determine efficacy and optimal dosages. There are several that could be used, but the most attractive is the Palmerston North Mouse. It has been shown that these mice, which all produce anti-dsDNA and develop nephritis, also develop anti-$U_1$RNP and Sm responses in almost all the animals with a dominant immune response against the A protein of $U_1$RNP measured in Western blot, as reported by Handwerger, et al., Clin. Res. 42:315A (1994). These mice have no detectable antibodies in the first three months of life but rapidly develop them after six months of age and experience a fulminant glomerulonephritis associated with anti-dsDNA antibodies. Dosage would range from 3 to 300 micrograms per mouse given weekly in the first experiments.

The same result obtained by administering peptide or a peptide conjugate can be achieved by coupling recombinant or isolated human ribosomal protein S1 to human IgG.

Although described herein with reference to the whole protein, it is preferable to use peptides of between a few amino acids up to about 100 amino acids, more preferably less than forty amino acids, still more preferably less than ten to twenty amino acids. These peptides can be easily ascertained by immobilizing the anti-dsDNA antibodies from a patient(s) and screening for binding of the peptides. Peptides can be prepared using standard techniques for amino acid synthesis or recombinantly, by engineering the cDNA (SEQ ID NO:1) encoding the protein, described in FIGS. 2 and 2a.

Anti-Id Antibodies that are Immunoeactive with Anti-dsDNA Antibodies

As demonstrated by Example 3, normal human sera contains anti-Id antibodies immunoreactive with anti-dsDNA antibodies present in many SLE patients. Antibodies for use in treating patients can be obtained using standard techniques to harvest antibodies from normal people, or, more preferably, antibody producing cells are isolated by binding of cells expressing antibody using a method as described in Example 3 for isolation of antibody. The antibody producing cells are then transformed with Eppstein-Barr virus (EBV), amplified in culture, the gene encoding the variable region of the anti-Id antibodies cloned, inserted into an appropriate vector, and expressed in bacteria or another appropriate expression system, using known techniques. Preliminary studies have yielded several clones.

In either case, antibody is administered to a patient in a dosage which decreases the amount of anti-dsDNA antibody. This is readily determined since SLE patients are routinely assayed for blood levels of anti-dsDNA. In most cases patients are expected to respond as they do to standard immunosuppressive therapy, by decreasing production of anti-dsDNA antibodies. In some cases, the antibodies will result in killing of the antibody producing cells in the patient. Treatments will be repeated as required.

An alternative approach is to screen recombinant libraries of Ig variable ("V") regions made from cDNA's reverse transcribed from mRNA extracted from peripheral blood lymphocytes from patients who produce anti-anti-dsDNA antibodies. A number of such libraries can be constructed and then screened for clones reactive with Fab anti-dsDNA but not normal Fab. These can then be used to produce any desired amount of anti-idiotype to anti-dsDNA. Alternatively, murine recombinant monoclonal anti-idiotypic antibodies directed against relevant idiotope(s) on anti-dsDNA can be produced.

This can be accomplished by the use of Pharmacia's (Pharmacia LKB Biotechnology, Sweden) "Recombinant Phage Antibody System" (RPAS), which generates a single-chain Fv fragment (ScFv) that incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans. The murine ScFv molecules can be "humanized" to further reduce the immunogenic stimulus presented.

Methods for "humanizing" antibodies, or generating less immunogenic fragments of non-human antibodies, are well known. A humanized antibody is one in which only the antigen-recognized sites, or complementarily-determining hypervariable regions (CDRs) are of non-human origin, whereas all framework regions (FR) of variable domains are products of human genes.

These "humanized" antibodies present a lesser xenograft rejection stimulus when introduced to a human recipient.

To accomplish humanization of a selected mouse monoclonal antibody, the CDR grafting method described by Daugherty, et al., *Nucl. Acids Res.*, 19:2471–2476, 1991, incorporated herein by reference, can be used. Briefly, the variable region DNA of a selected animal recombinant anti-idiotypic ScFv is sequenced by the method of Clackson, T., et al., *Nature*, 352:624–688, 1991, incorporated herein by reference. Using this sequence, animal CDRs are distinguished from animal framework regions (FR) based on locations of the CDRs in known sequences of animal variable genes. Kabat, H. A., et al.l, *Sequences of Proteins of Immunological Interest*, 4th Ed. (U.S. Dept. health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CRDs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The present invention will be further understood by reference to the following examples.

EXAMPLE 1

Anti-dsDNA Antibodies are Cross-reactive with Human Ribosomal Protein S1

It has been reported that anti-dsDNA antibodies cross-react with a number of proteins (5–12). However, no one has reported using human anti-dsDNA antibodies as probes to clone cDNAs which encode proteins recognized by anti-dsDNA antibodies. A cDNA clone that encodes human ribosomal protein S1 which is recognized by anti-dsDNA antibodies from SLE patients has been isolated using this method.

Materials and Methods

Abbreviations:

SLE, systemic lupus erythematosus; Anti-dsDNA(AP) and anti-dsDNA(IK), affinity-purified anti-dsDNA antibodies from patient sera AP and IK; GST, glutathione S-transferase; Kd, dissociation constant; TBS, tris-buffered saline; IFA, indirect immunofluorescence; G7-FP, GST-fusion protein expressed by G7; G7-RP, recombinant protein expressed by G7; r-proteins, ribosomal proteins; ES1, *E.coli* ribosomal protein S1; HS1, human ribosomal protein S1

Sera

Affinity-purified anti-dsDNA antibodies were eluted from DNA cellulose column (Sigma Chemical Company, St. Louis, Mo.) as described by Reichlin, et al., *J. Clin. Invest.* 93:443 (1994). Ten SLE patient sera containing anti-dsDNA antibodies, two samples of affinity-purified anti-dsDNA antibodies from patient sera AP and IK [anti-dsDNA(AP) and anti-dsDNA(IK), respectively], and 2 human IgG monoclonal anti-dsDNA antibodies (33.C9 and 33.H11) (Winkler, et al. *Clin. Exp. Immunol.* 85:379 (1991)) were used for characterizing cDNA clones. The isotypes and light chains of 33.C9 and 33.H11 were IgG2 (kappa) and IgG1 (lambda), respectively. Both of these monoclonal anti-dsDNA antibodies were derived from one SLE patient serum. Anti-dsDNA antibodies were detected by the Crithidia assay (Aarden, et al., Ann. *NY Acad. Sci.* 254:505 (1975)).

Screening of cDNA Libraries

A phage lambda gt11 cDNA library constructed from mRNA of human liver (Clontech Laboratories Inc., Palo Alto, Calif.) was screened as described by Young and Davis, *Proc. Natl. Acad. Sci. USA* 80:1194 (1983) with a SLE patient (LG) serum which contained a high titer of anti-dsDNA antibody. Serum LG also contained anti-U1RNP and anti-Ku antibodies. A positive plaque was sequentially subcloned until all progency plaques were recognized by the serum.

Preparation of Glutathione S-transferase Fusion Protein and Recombinant Protein, Western Blot EcoRI-digested cDNA insert isolated from the recombinant phage was ligated into EcoRI-digested pGEX-1λT expression vector (Pharmacia LKB Biotechnology Inc., Uppsala, Sweden). The glutathione S-transferase (GST) fusion protein was expressed in *E. coli* and purified by using glutathione sepharose 4B as described by Smith, et al., *Gene* (Amst.) 67:31 (1988). The GST carrier protein was removed by thrombin proteolysis to isolate the recombinant protein. Western blot was performed as described by Itoh, et al., *Clin. Exp. Immunol.* 81:45 (1990). In Western blot, alkaline phosphatase-conjugated goat-anti-human IgG (Sigma Chemical Company, St. Louis, Mo.) was used as the second antibody. Patient sera were diluted to 1:100 for use in Western blot.

Treatment of Sera with DNAse I

To treat the sera with DNAse I, sera were incubated with 10 μg/ml of DNAse I (Sigma Chemical Company, St. Louis, Mo.) for 1 H at 37° before incubating with nitrocellulose (NC) membranes in Western blot.

Inhibition Western Blot

Inhibition Western blot reactivity of the sera against the GST-fusion protein was accomplished by preincubating with appropriate dilutions of the sera for 3 h at room temperature with 0, 5, 10, 50, or 100 μg/ml of calf thymus dsDNA or Yeast tRNA (Sigma Chemical Company, St. Louis, Mo.) before incubating the sera with NC membranes bound GST-fusion protein.

Inhibition ELISA

Purified recombinant protein (5.0 μg/ml in 0.05 M carbonate bicarbonate buffer, pH 9.6) was coated on a microtiter plate well (Costar, Cambridge, Mass.) by incubating overnight at 4° C. For coating the plates with DNA, 0.5 mg/ml of protamine sulfate was precoated by incubating for 3 h at room temperature. After washing twice with 0.05% Tween 20 in PBS, 20 μg/ml of calf thymus dsDNA (Sigma Chemical Company, St. Louis, Mo.) was coated by incubating overnight at 4° C. Appropriate dilutions of the sera were preincubated with different concentrations of the recombinant protein, BSA, calf thymus dsDNA, or Yeast tRNA (Sigma Chemical Company, St. Louis, Mo.) for 3 h at room temperature before applying the sera to the plates. After blocking the plates with 0.1% BSA in PBS (4° C., overnight), preincubated sera were added and incubated (4° C., overnight). After washing 5 times with 0.5% Tween 20 in PBS, alkaline phosphatase-conjugated goat anti-serum IgG (Sigma Chemical Company, St. Louis, Mo.) was added and incubated (4° C., overnight). After washing 5 times with 0.05% Tween 20 in PBS, p-nitrophenyl phosphate substrate solution was added and the OD at 405 nm as measured. % inhibition was defined as follows; % inhibition=

$$\frac{OD \text{ without inhibitor} - OD \text{ with inhibitor}}{OD \text{ without inhibitor}} \times 100$$

Calculation of Dissociation Constant of Antibodies

The dissociation constant (Kd)[3] were calculated by Scatchard analysis as described by Friquet et al., *J. Immunol. Methods.* 77:305 (1985).

Preparation of MOLT4 Cell Extract

MOLT4 cells were collected, washed twice with 0.02M Tris-buffered saline (TBS), and were resuspended in 0.01M Tris-HCl, 0.015M NaCl, 0.0% Nonidet P-40, pH 7.2. After centrifugation at 10,00 g for 15 min, the supernatant was used as MOLT4 cell extract.

Affinity Purification of Antibodies Bound the GST-fusion Protein

After the purified GST-fusion protein was electrophoresed and transferred to NC membranes, membranes were blocked with 5% skim milk solution in TBS. Membranes were then incubated with a patient serum LG for 2 h at room temperature. After washing 3 times with 0.05% Tween 20 in TBS, membrane-bound antibodies were eluted by 0.5M glycine-HCl, pH 2.9, neutralized by adding Tris base, and then concentrated using CENTRICON™ 30 concentrator (Amicon Division, W. R. Grace, Denvers, Mass.). These purified antibodies were used as probes for Western blot using MOLT4 cell extract.

DNA Sequencing

A cDNA insert isolated from a recombinant phage (EcoRI fragments) was digested with several restriction enzymes (Bgl II, EcoRV, Pst I, and Sau3A I; Promega Corp., Madison, Wis.) and the resulting DNA fragments were ligated into the polylinker regions of M13mp18 replicative form DNA. Nucleotide sequences were determined by using the dideoxychain termination method (Sanger, et al. *Proc. Natl. Acad. Sci. USA* 74:5463 (1977)) with T7 DNA polymerase (Dale, et al. *Plasmid* 13:31 (1985)) (U.S. Biochemical Corp., Cleveland, Ohio). Nucleotide and amino acid sequence were analyzed using the Sequence Analysis Software Package of the Genetics Computer Group, University of Wisconsin (Devereux, et al., *Nucleic Acids Res.* 12:387 (1984)) on a VAX 8250 computer.

Inhibition Immunofluorescence

Appropriate dilutions of 33.C9 and 33.H11 were preincubated with 0, 1.0, 10, 100, or 1,000 μg/ml of the recombinant protein, BSA, calf thymus dsDNA, or Yeast tRNA overnight at 4° C. before applying the antibodies for indirect immunofluorescence (IFA)[3] using Hep 2 cells. IFA using Hep 2 cells (INOVA Diagnostics, Inc., San Diego, Calif.) was performed as described by Gonzalez, et al., *N.Eng. J. Med.* 274:1333 (1966). FITC-labelled goat anti-human IgG (Sigma, Chemical Company, St. Louis, Mo.) was used at the second antibody.

Results

Isolation and Characterization of a cDNA Encoding a Protein Bound by Anti-dsDNA Antibody Using a SLE patient (LG) anti-dsDNA serum as a probe, 1×10[6] clones of the human liver cDNA library in lambda gt11 phage were screend and one positive clone (termed G7) obtained. This clone was recognized by anti-dsDNA antibodies [anti-dsDNA antibody-positive patient sera LG and AC, anti-dsDNA (AP), and anti-dsDNA(1K) anti-bodies] when the β-galactosidase fusion protein was induced by isopropyl thiogalactoside. On the other hand, normal control, anti-Ku, and anti-U1RNP antibody-positive sera did not react with this fusion protein. EcoRI-digestion of the recombinant phage DNA demonstrated a 1.3-kb cDNA insert in G7.

To express the GST-fusion protein, the cDNA insert was then ligated into pGEX-1λT expression vector. A Western blot of the GST-fusion protein expressed by G7(G7-FP) was carried out. G7-FP (66 kDa) was electrophoresed (10% polyacrylamide gel) and transferred to nitrocellulose membranes. NC membranes were incubated with following sera; Anti-dsDNA patient sera LG, BK, JP, WC, JH, RP, CC, JC, BJ, and AC, anti-dsDNA(AP), anti-dsDNA(IK), 33.C9, 33.H11, normal control serum, and anti-U1RNP/Sm antibody serum IA. As shown on the Western blot, all the 10 patient sera containing anti-dsDNA antibodies (diluted to 1:100), both of the affinity-purified anti-dsDNAs (6.6 μg/ml), and both of the IgG human monoclonal anti-dsDNA antibodies (27 μg/ml of 33.C9 and 1.8 μg/ml of 33.H11) recognized the 66 kDa GST-fusion protein expressed by G7 (G7-FP)[3] (28 kDa of 66 kDa is the GST portion and 38 kDa is expected to be the recombinant part encased by G7). None of them reacted with GST carrier protein which was expressed in E. coli transformed with non-insert pGEX-1λT vector on Western blot. Inhibition of antibody binding to the GST-fusion protein or the recombinant protein by DNA was demonstrated by Western blot. G7-FP (66 kDa) was electrophoresed (10% polyacrylamide gel) and transferred to NC membranes. 33.C9 (0.27 μg/ml) was preincubated with 0, 5, 10, 50, or 100 μg/ml of calf thymus dsDNA or Yeast tRNA before incubating with NC membranes. As demonstrated by the Western blot, 33.C9 recognized G7-FP even if 33.C9 is diluted to 0.27 μg/ml. As there is a possibility that anti-dsDNA antibodies bind to DNA in sera and this DNA which made complexes with anti-dsDNA antibodies binds to G7-FP, anti-dsDNA antibodies [33.C9 (27 μg/ml) and serum LG (diluted to 1:100)] were treated with DNAse I. Treatment by DNAse I did not decrease the reactivity of these antibodies against G7-FP on Western blot. This result shows that anti-dsDNA antibodies react directly with G7-FP.

To establish the specificity of antibodies which recognize the 66 kDa G7-FP in Western blot as anti-dsDNA antibodies, 33.C9 (0.27 μg/ml) was preincubated with different concentrations of calf thymus dsDNA or Yeast tRNA before incubating with the NC membrane bound G7-FP. The reactivity of 33.C9 against G7-FP was inhibited by 5 μg/ml of DNA but not by RNA.

G7-GP was proteolysed with thrombin to isolate the recombinant protein (G7-RP). Polyacrylamide/NaDodSO₄ gel electrophoresis (SDS-PAGE) and Western blot analysis of Gy-RP solution showed that only one recombinant protein band (42 kDa) was seen and was recognized by anti-dsDNA antibody-positive patient serum LG, anti-dsDNA (AP), anti-dsDNA (IK), 33.C9, and 33.H11 but was not recognized by normal control, anti-U1RNP, nor anti-Ku antibody-positive sera. Thus, one can conclude that this recombinant protein solution contains only G7-RP and has antigenicity.

The inhibition of antibody binding to G7-RP by DNA was also examined in ELISA (FIG. 1). Two anti-dsDNA antibody-positive patient sera (LG and JP diluted to 1:10⁴), affinity-purified anti-dsDNA antibodies [anti-dsDNA(AP) and anti-dsDNA(IK), both of which were 0.33 μg/ml, and 33.H11 (0.0071 μg/ml) were pre-incubated with different concentrations of calf thymus dsDNA or Yeast tRNA before adding these antibodies to the plates coated with G7-RP. Reactivity of all these anti-dsDNA antibodies was inhibited almost completely (% inhibition greater than 90%) by DNA but not by RNA.

These results suggest that antibodies which recognizes G7-FP or G7-RP are anti-dsDNA antibodies.

Reactivities of the Affinity-purified Antibodies Eluted from G7-FP with MOLT4 Cell Extract.

G7-FP-transferred NC membrane was incubated with serum LG. The antibodies that bound G7-FP from this NC membrane were eluted. This affinity-purified antibody at concentration of 5 μg/ml was positive for anti-dsDNA antibody by the Crithidia assay and recognized G7-FP on Western blot.

The affinity-purified antibody eluted from G7-FP was used as a probe in Western blot to identify the responsible protein which the cDNA insert in G7 encodes. Reactivity of the affinity-purified antibody eluted from G7-FP with MOLT4 cell extract was determined by SDS-PAGE (5.5% polyacrylamide gel) transferred to NC membranes. The NC membranes were incubated with normal control serum, affinity-purified antibody eluted from G7-FP, patient sera LG, AC, and JP, anti-dsDNA(AP), anti-dsDNA(IK), 33.C9, anti-U1RNP patient serum YN, and anti-Ku patient serum HK. A common protein band (104 kDa) was recognized by all the anti-dsDNA antibodies and the affinity-purified antibody eluted from G7-FP. The affinity-purified antibody (from serum LG) at a concentration of 5 μg/ml eluted from G7-FP reacted only with this 104 kDa protein.

On the other hand, normal control, anti-U1RNP, and anti-Ku antibody-positive sera did not react with this protein. Also in Western blot with 12.5% polyacrylamide gel using MOLT4 cell extract, the affinity-purified antibody eluted from G7-FP recognized only this 104 kDa protein and this protein band was commonly reactive with anti-dsDNA antibodies (not shown). Thus, it appears that this 104 kDa protein at least in MOLT4 cell extract is the responsible protein of which G7 encodes a portion.

Sequence Analysis of the cDNA Insert in G7

The nucleotide sequence of the cDNA insert in G7 was determined. Its primary nucleotide (SEQ ID NO:1) and deduced amino acid (SEQ ID NO:2) sequences (GenBank no. U27517) are shown in FIGS. 2 and 2a. The cDNA insert (SEQ ID NO:1) proved to be 1,314 nucleotides in length. The TAA stop codon is located at positions 1057–1059. The predicted molecular weight for the encoded polypeptides (SEQ ID NO:2) (352 amino acids) is 38.0 kDa. However, this cDNA insert (SEQ ID NO:1) in G7 seems to be a partial length cDNA because the molecular weight of the encoded polypeptide (SEQ ID NO:2) is smaller than the estimated full length size (104 kDa) of the reactive protein in MOLT4 cell extract. Thus, this cDNA (SEQ ID NO:1) does not seem to contain the initiation codon.

A search for similarities between the nucleotide sequence of the cDNA (SEQ ID NO:1) in G7 (GenBank no. U27517) and other sequences through the NCBI using the BLAST network service showed a significant match (99% identity) with a sequence encoding human ribosomal protein (r-protein) S1 homologue mRNA reported by Eklund at al., *Gene* 155:231 (1995) (SEQ ID NO:3). However, there are 3 nucleotide and 1 amino acid differences between the G7 cDNA insert (SEQ ID NO:1) and their cDNA sequence (SEQ ID NO:3) (GTC (positions 130–132) in the G7 cDNA insert (SEQ ID NO:1) vs GTA (positions 292–294) in their cDNA (SEQ ID NO:3), AGT (positions 133–135, encodes Ser at residue 45) in the G7 cDNA insert (SEQ ID NO:1) vs GCT (positions 295–297, encodes Ala at residue 99) in their cDNA (SEQ ID NO:3)]. Moreover, 2 nucleotides (C at positions 1355 and 1366) and 162 nucleotides (positions 1–162) in their cDNA (SEQ ID NO:3) are deleted in the G7 cDNA insert (SEQ ID NO:1). A search was made for some similarities between the predicted amino acid sequence (SEQ ID NO:2) and other protein sequences in the SWIS-SPROT database using the algorithm as described by Gish, et al., *Nature Genetics* 3:266 (1993); Altschul, et al., *J. Mol. Biol.* 215:403 (1990).

High Degree of Homology Between the Central Core Region (residues 63–317) of the Predicted Amino Acid (SEQ ID NO:2) of this Protein and those of Several r-proteins S1.

Identify and similarity with r-proteins S1 are the following; 39% identity and 65% similarity with *E. coli* r-protein S1 (ES1) (SEQ ID NO:4) (26), 40% identity and 64% similarity with Providencia sp. r-protein s1 (PS1) (SEQ ID NO:6) (Schnier, et al., *Mol. Gen. Genet.* 200:476 (1985)), 38% identity and 63% similarity with *Rhizobium melilotti* r-protein S1 (RS1) (SEQ ID NO:5) (Schnier, et al., *Nucleic Acids Res.* 16:3075 (1988)), and 50% identity and 71% similarity with chloroplast r-protein S1 (CS1) (SEQ ID NO:7) (Franzetti, et al., *J. Biol. Chem.* 267:19075 (1992)). Moreover, 5 repeating regions [EGTV (SEQ ID NO:8) (residue 158–161 and 243–246), DFGAFV (SEQ ID NO:9) (166–171 and 251–256), GLVHVS (SEQ ID NO:10)

(178–183 and 264–269), GDKV (SEQ ID NO:11) (200–203 and 286–289), and RISLS (SEQ ID NO:12) (216–220 and 302–306)] were observed in the protein sequence (SEQ ID NO:2). These repeating residues (SEQ ID NOS:8 to 12) have a high degree of homology among other r-proteins S1 (FIG. 3).

Inhibition Immunofluorescence

Inhibition of indirect immunofluorescence was measured using Hep 2 cells. Staining of Hep 2 cells by 33.H11 or 33.C9 without preincubation, after preincubation with G7-RP [100 μg/ml for 33.H11 or 1,000 μg/ml for 33.C9], or after preincubation with calf thymus dsDNA [1,000 μg/ml for 33.H11 or 1.0 μg/ml for 33.C9]. 33.H11 (0.18 μg/ml) without inhibitor added showed cytoplasmic and nucleolar staining pattern while 33.C9 (1.7 μg/ml) showed homogenous nuclear staining pattern in IFA. After preincubating with from 1.0 to 1,000 μg/ml of BSA or RNA as negative controls, these staining patterns were not changed or diminished. The staining pattern of 33.H11 was inhibited by 100 and 1,000 μg/ml of G7-RP and by 1,000 μg/ml of calf thymus dsDNA while that of 33.C9 was inhibited by from 1.0 to 1,000 μg/ml of calf thymus dsDNA but not by any concentration of G7-RP.

Figure 4A:
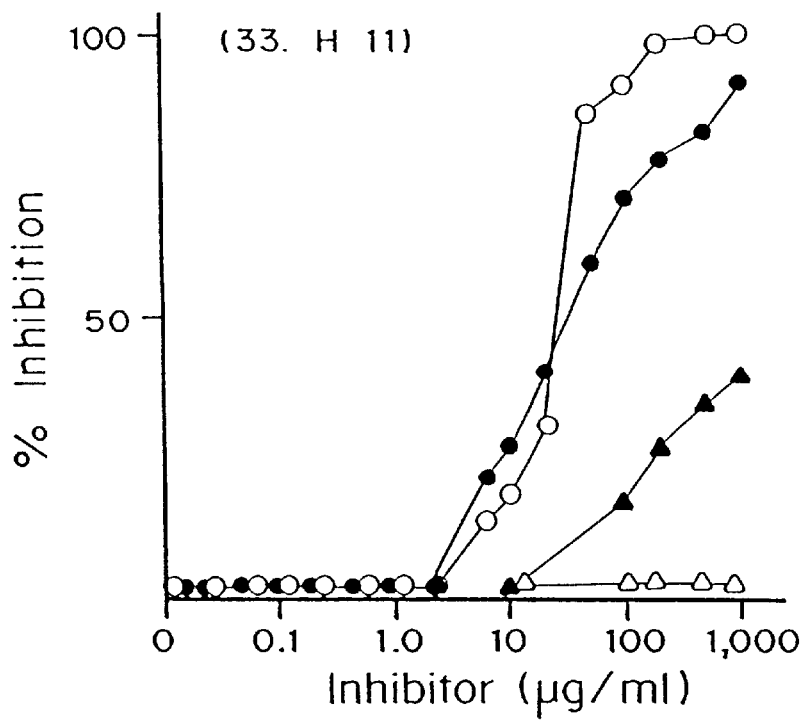
FIGS. 4A–D are graphs comparing the affinity of 33.H11 and 33.C9 for G7-RP or DNA in inhibition ELISA. 33.H11 [A (0.0031 µg/ml) and C (1.0 µg/ml)] and 33.C9 [B (0.32 µg/ml) and D (0.56 µg/ml)] were preincubated with different concentrations of calf thymus dsDNA (●), G7-RP (○), Yeast tRNA (▲), or BSA (Δ), before adding the antibodies to the plates coated with calf thymus dsDNA (A and B) or G7-RP (C and D).
Figure 4B:
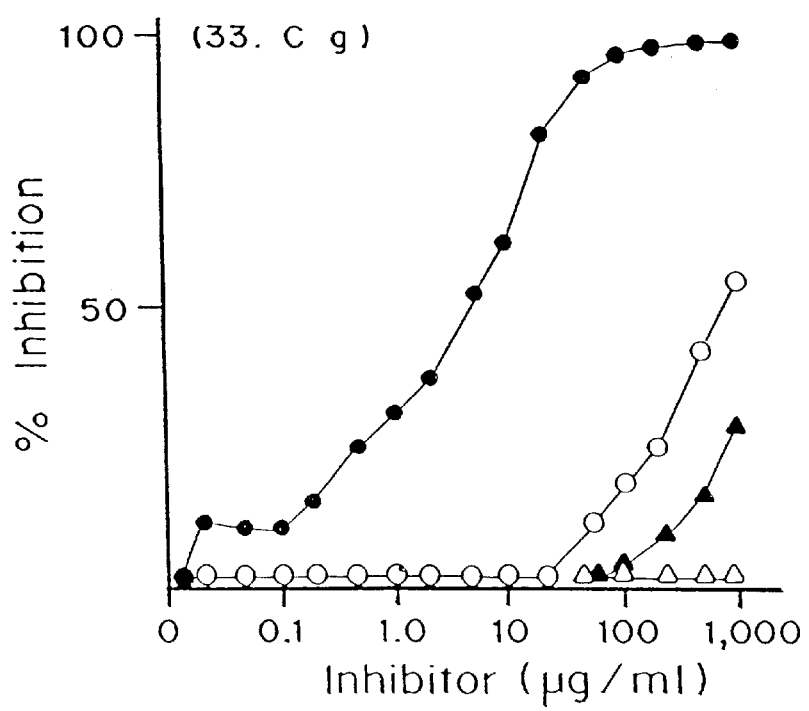
Figure 4C:
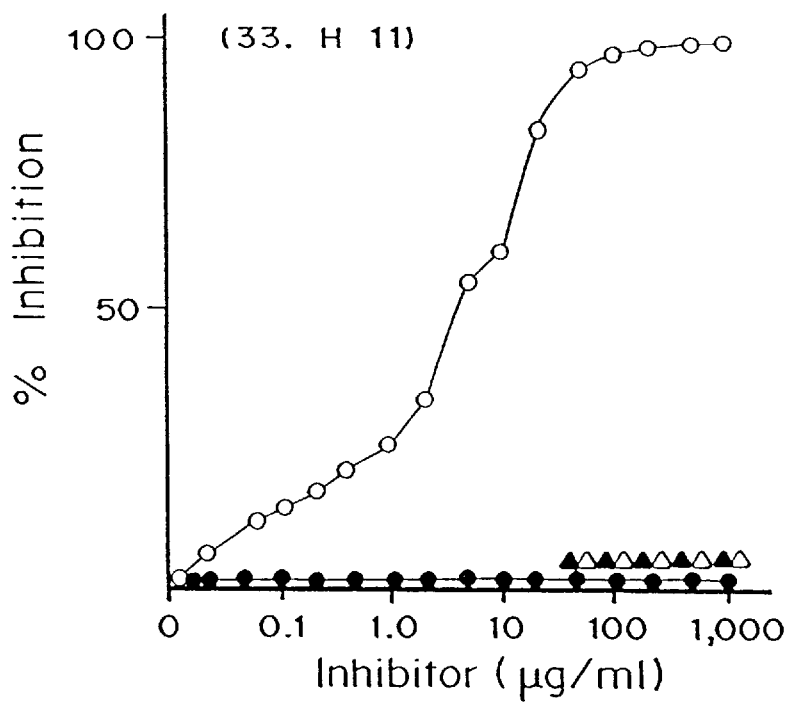
Figure 4D:
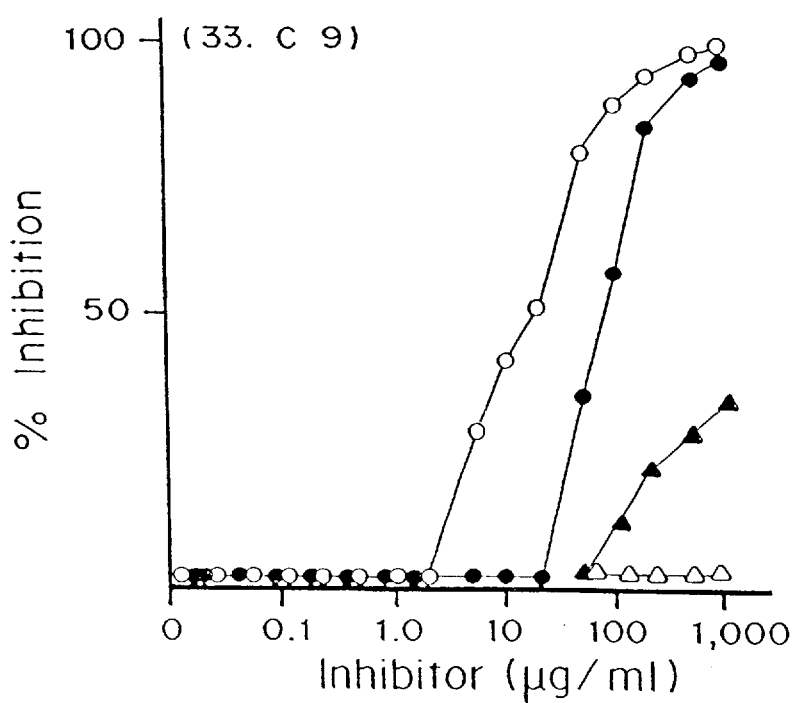

Comparison of the Affinity of 33.h11 and 33.C9 Against G7-RP or DNA by Inhibition ELISA The inhibition of 33.H11 and 33.C9 binding to G7-RP by DNA was compared or reciprocally binding to DNA by G7-RP in inhibition ELISA (FIGS. 4A–D). 33.H11 was diluted to 0.0031 μg/ml and 1.0 μg/ml while 33.C9 was diluted to 0.32 μg/ml and 0.56 μg/ml for ELISA using calf thymus dsDNA and G7-RP as antigens, respectively. These antibody concentrations were used as they gave 75% of the maximum OD for the ELISA coated with calf thymus dsDNA or G7-RP when saturating amounts of antibody were used. These antibodies were preincubated with from 0 to 1,000 μg/ml of G7-RP, calf thymus dsDNA, bSA, or Yeast tRNA. The binding of 1.0 μg/ml of 33.H11 to Gy-RP was not inhibited by DNA (FIG. 4C) while the binding of 33.C9 was inhibited completely by DNA (FIG. 4D). On the other hand, in an ELISA with DNA-coated plates, the inhibition of 33.C9 by G7-RP was far less effective (FIG. 4B) compared with that of 33.H11 (FIG. 4A), as about 100 times more G7-RP was required for inhibition. These data suggest that 33.H11 binds G7-RP more strongly than does 33.C9 while 33.C9 binds DNA more strongly than does 33.H11.

Kd Value of 33.C9 and 33.H11 for G7-RP or DNA

From the data of the inhibition ELISA coated with G7-RP (described as the open circles in FIGS. 4C and 4D) and calf thymus dsDNA (described as the closed circles in FIGS. 4A and 4B), the Kd value of each monoclonal anti-dsDNA antibody was calculated for G7-RP and calf thymus dsDNA as the ligands, respectively.

Before the calculation of Kd, average molecular weight of the monomeric unit of calf thymus dsDNA were determined because the size of calf thymus dsDNA is heterogeneous. If % inhibition/100 on the inhibition ELISA is defined as v, $K_D$ (dissociation constant) can be rewritten from the Scatchard equation (Friguet, et al. 1985) as follows;

$$K_D = a_o - i_o v)(1/v - 1)$$

where $a_o$ and $i_o$ are the total concentration of the inhibitor (mol/l) and the total antibody concentration (mol/l), respectively. Therefore, if % inhibition at two different concentrations of the inhibitor added and $i_o$ are known, $a_o$ (mol/l) and molecular weight of the inhibitor can be determined even if $K_D$ is unknown. As a result, the average molecular weight of the monomeric unit of calf thymus dsDNA was $1.0 \times 10^6$.

$K_d$ values of 33.c9 and 33.H11 for G7-RP or DNA were calculated by Scatchard plots. 42,000 was used as the molecular weight of G7-RP. As shown in Table I, the $K_d$ value of 33.H11 for G7-RP was lower than that for DNA. On the other hand, $K_d$ value of 33.C9 for DNA was two magnitudes lower than that for G7-RP. As affinities are inversely proportioned to the Kd value, these data suggest that 33.H11 has a higher affinity for G7-RP than for DNA while 33.C9 has a much higher affinity for DNA than for G7-RP. These differences of affinities correlate with the different staining patterns of IFA exhibited by the 2 monoclonal anti-dsDNA antibodies. In that view, 33.h11 binds the cytoplasm plus nucleolus where one would expect the r-protein S1 to be localized and 33.C9 binds the nucleus where DNA is localized.

TABLE I

Kd (dissociation constant) (mol/l) of the two human IgG monoclonal anti-dsDNA antibodies for calf thymus dsDNA or G7-RP.

| antibodies | calf thymus dsDNA | G7-RP |
|---|---|---|
| | ligand | |
| 33.H11 | $1.0 \times 10^{-7}$ | $6.5 \times 10^{-8}$ |
| 33.C9 | $3.0 \times 10^{-9}$ | $3.9 \times 10^{-7}$ |

Discussion

In summary, a lambda gt11 cDNA library constructed from mRNA of human liver was screened by using a SLE patient serum with anti-dsDNA antibody and a clone G7 which has a 1.3-kb cDNA insert (SEQ ID NO:1) isolated. Not only all of the 10 anti-dsDNA patient sera but also affinity-purified anti-dsDNA and human IgG monoclonal anti-dsDNA antibodies recognized the protein expressed by G7. The affinity-purified antibody eluted from this protein was positive for anti-dsDNA antibody activity by the Crithidia assay. Moreover, antibody binding to this protein was inhibited completely by DNA but not by RNA. From those observations, it was concluded that anti-dsDNA antibodies cross-react with the protein expressed by G7.

A significant match (99% identify) between the nucleotide sequence of the cDNA in G7 (SEQ ID NO:1) and a cDNA reported by Eklund et al. as encoding human r-protein S1 homologue mRNA was found. It appears that anti-dsDNA antibodies directly bind to the protein expressed by G7 because the reactivity of anti-dsDNA antibodies against the protein was not influenced by DNAase I treatment and the binding of anti-dsDNA antibodies to the protein was inhibited completely by DNA. The predicted amino acid sequence (SEQ ID NO:2) presented in this study had homology with some r-proteins S1 including ES1 (SEQ ID NO:4). ES1 (SEQ ID NO:4) is well characterized at the functional and structural level (Subramanian, *Prog. Nucleic Acids Res. Mol. Biol.* 28:101 (1983)) while there are few reports about mammalian r-proteins S1. ES1 (SEQ ID NO:4) is the largest protein of the ribosome and has the same length as the ribosome. This protein is associated with the 30S ribosomal subunit in prokaryotes via its N-terminal globular domain and is known to stimulate translation by facilitating mRNA binding to the 30S ribosomal subunit. The central and C-terminal region contain repeating homologous sequences which are known to play a key role in the binding of structural elements of r-protein S1 to mRNA. Five repeating regions (EGTV (SEQ ID NO:8), DFGAFV (SEQ ID NO:9), GLVHVS (SEQ ID NO:10), GDKV (SEQ ID NO:11) and RISLS (SEQ ID NO:12) which repeat twice in the central core region of the protein (SEQ ID NO:2) were observed (FIG. 3). This apparent gene duplication which encodes this repeat region is absent only in the chloroplast r-protein S1.

Cytoplasmic and nucleolar staining patterns in IFA suggests that the antigenic target is the ribosome. This is the IFA pattern of human monoclonal anti-dsDNA antibody 33.H11 which is inhibited by both 100 µg/ml of G7-RP and higher concentrations (1,000 µg/ml) of DNA. These results show that G7 encodes a ribosomal protein which is recognized by anti-dsDNA antibodies. From these observations, it is concluded that G7 encodes a part of human r-protein S1 (HS1).

It has been reported that anti-dsDNA antibodies have high frequencies of basic amino acids carrying positive charges in the heavy chain complementarity determining regions and that arginine is the most versatile amino acid for binding with negative-charged DNA (31). However, there are no high scoring negative charged segments, which could be an epitope for anti-dsDNA antibody, in the primary sequence of HS1. These observations might suggest that cross-reactions between anti-dsDNA antibody and HS1 are not dependent on charge interaction in the primary sequence alone but rather that the cross-reactive epitope depends on conformational apposition of negative charges in the tertiary structure of HS1. However, it is likely that HS1 mimics DNA because anti-dsDNA antibodies cross-react with HS1. It is also appealing to believe that proteins which "mimic" the structure of DNA could play a role as immunogen.

Both 33.H11 and 33.C9 are IgG monoclonal anti-dsDNA antibodies (Winkler, et al., *Clin. Exp. Immunol.* 85:379 (1991)) and strongly recognized the protein expressed by G7.However, in IFA, 33.H11 did not show a homogeneous nuclear pattern and the homogeneous nuclear staining patterns of 33.C9 was not inhibited by G7-RP but was inhibited by as little as 1.0 µg/ml of DNA. Also in ELISA, much lower concentrations of DNA were able to inhibit the binding of 33.C9 to G7-RP compared with that of 33.H11 while much higher concentrations of G7-RP were needed to inhibit the binding of 33.C9 to DNA compared with that of 33.H11. Although the binding of 33.H11 (1.0 µg/ml) to G7-RP did not seem to be inhibited even by 1,000 g/ml of DNA (FIG. 4C), that of 33.H11 (0.0071 g/ml) to G7-RP were inhibited completely by DNA (FIG. 1). Therefore, it is likely that this concentration (1.0 g/ml) of 33.H11 in FIG. 4C is too high to be inhibited by DNA. Analysis of $K_d$ value showed that 33.H11 has a higher affinity for HS1 than for DNA while 33.C9 has a higher affinity has a higher affinity for DNA than for HS1. In most anti-dsDNA-positive SLE patient sera, anti-dsDNA antibodies behave like 33.C9 which has a higher affinity for DNA than for HS1 but indeed recognizes HS1. Anti-dsDNA antibodies of this type likely predominate because such sera rarely show a cytoplasmic and nucleolar staining pattern but rather a classical nuclear pattern in IFA as does 33.C9.

Yanase, et al. *Lab. Invest.* 71:52 (1994), have reported that anti-dsDNA antibodies penetrate living cell membranes and bind to cytoplasmic proteins before binding to the nucleus. From these standpoint, anti-dsDNA antibodies like 33.H11 recognize HS1 strongly and are trapped in the cytoplasm preventing their entry into the nucleus. In studies with living PK15 cells, 33.H11 penetrates the plasma membrane and indeed localizes in the cytoplasm.

IT is assumed that most of the amino acid sequences which G7 encodes are mRNA-binding sites on HS1 because five repeating regions (SEQ ID NOS:8 to 12) (residues 158–306) which repeat twice in HS1 (SEQ ID NO:3) and are supposed to be a feature of the mRNA binding site are observed. Therefore, if anti-dsDNA antibodies like 33.H11 bind to mRNA-binding portions on HS1, these anti-dsDNA antibodies might block the binding of mRNA to 40S (eukaryotes) ribosomal subunit, that is, the initiation reaction of translation.

EXAMPLE 2

Suppression of Protein Synthesis by Anti-dsDNA Antibodies Cross-reactive with Ribosomal Protein S1

Four systemic lupus erythematosus (SLE) patient sera containing anti-dsDNA Antibodies, 3 affinity-purified anti-dsDNA IgG, and a human monoclonal anti-dsDNA Ab (33.H11) immunoprecipitate 18S ribosomal RNA from DNase-treated $^{32}$P-labeled MOLT4 cell extract. This 18S RNA precipitation was inhibited completely by preincubating 33.H11 with calf thymus dsDNA or the recombinant human ribosomal protein Si, which was described in Example 1 as cross-reactive with anti-dsDNA antibodies. 33.H11 did not immunoprecipitate 18S RNA when deproteinized labeled cell extract was used as the antigen. Whole IgG from 3 SLE sera with anti-dsDNA Antibodies, 33.H11, and 3 affinity-purified anti-dsDNA IgG inhibited in vitro translation of globin mRNA (% inhibition was 36–50%). This translation inhibition by anti-dsDNA Antibodies was enhanced (67–79%) when the reticulocyte lysate was treated with DNase. Suppression of protein synthesis is thereby indicated as a pathogenic mechanism of anti-dsDNA Antibodies. The r-protein S1 in *E. coli* is well known to be associated with the 30S ribosomal subunit via its N-terminal globular domain. This protein has mRNA-binding sites and plays a key role in transaction initiation by binding to mRNA in *E. coli*. In this study, anti-dsDNA Antibodies were shown to immunoprecipitate 18S ribosomal RNA and suppress in vitro translation of mRNA. These date are the first to demonstrate inhibition of in vitro protein synthesis by anti-dsDNA Antibodies.

Materials and Methods

Recombinant r-protein S1

Recombinant r-protein S1 (42 kDa) expressed from G7 clone (G&-RP) was prepared as described in Example 1.

RNA Immunoprecipitation (RNA-IP)

A procedure based on that of Matter, et al. *Arthritis Rheum.* 25:1278 (1982) was used. MOLT4 cells (2×10$^6$ cells) were labeled with 100 µCi of $^{32}$P-phosphate (ICN Pharmaceuticals Inc., Costa Mesa, Calif.) in RPMI 1640 medium (phosphate-free) for 16 h. Cells were washed with Tris-buffered saline (TBS), lysed in 0.01 M tris-HCl, pH 7.2, 0.145 M NaCl, 0.5% Nonidet P-40 (NP-40) for 20 min, and centrifuged at 10,000 g for 10 min. After centrifugation, 100 µl of the supernatant was incubated with 10 units of RQ1 DNase (RNase-free) (Promega Corp., Madison, Wis.) for 30 min at 37° C. and was used as the labeled cell extract. Two mg of Protein A SEPHAROSE 4B™ (Pharmacia LKB Biotechnology Inc., Uppsala, Sweden) preswollen in 500 µl of NET-2 (0.01 M tris, 0.15 M NaCl, pH 7.5, 0.05% NP-40) was incubated with an appropriate amount of antibodies (10 µl for a serum) for 15 h at 4° C., and then washed 5 times with NET-2. The antibody-bound beads were incubated for 2 h at 4° C. with the labeled cell extract. After 5 washes with NET-2, the beads were incubated with 1 unit of RQ1 DNase for 30 min at 37° C. Precipitated RNAs were extracted by phenol extraction and ethanol precipitation and analyzed on polyacrylamide non-denaturing gel electrophoresis (2.5% acrylamide, 0.04 M Tris-acetate, pH 7.8, 0.02 M NaOAc, 0.002 M EDTA) (Loening, *Biochem. J.* 102:251 (1967)) followed by audioradiography.

In experiments designed to test whether proteins are necessary for antibodies to precipitate RNAs, labeled cell extract was deproteinized by phenol extraction and ethanol precipitation and then resuspended in 100 µl of NET-2 before RNA-IP was performed as described above.

Inhibition of Immunoprecipitating Ability of 33.H11 by dsDNA or G7-RP

A quantity (0.1 µg) of the human IgG monoclonal anti-dsDNA Ab 33.H11 (Winker, et al. 1991) was preincubated in 500 µl of NET-2 with 100 µg/ml of calf thymus dsDNA (or Yeast tRNA as a negative control) or 100 µg/ml of G7-RP (or BSA as a negative control) before RNA-IP was performed as described above. For RNA-IP by 33.H11 which was preincubated with calf thymus dsDNA or Yeast tRNA, labeled cell extract and washed beds were not treated with RQ1 DNase.

Anti-dsDNA Sera and Purification of IgG

Anti-dsDNA antibodies were detected by the Crithidia assay or ELISA. For the affinity-purification of anti-dsDNA IgG, SLE patient sera containing anti-dsDNA antibodies were applied to DNA cellulose columns (Sigma Chemical Company, St. Louis, Mo.) as described above and the eluate was incubated with 10 mg of Protein A Sepharose 4B in TBS for 15 h at 4° C. After washing 5 times with TBS, IgG was eluted from the Ab-bound beads with 0.2 M glycine-HC1, pH 3.0 and concentrated after neutralization.

For purifying whole IgG from patient sera or for 33.H11 IgG, 50 µl of patient sera or 1 ml of the supernatant from the hybridoma cell culture for 33.H11 were incubated with 10 mg of Protein A Sepharose 4B and IgG was eluted as described above. Five SLE patient sera containing anti-dsDNA antibodies which are positive with the Crithidia assay [LG(anti-U1RNP) +), AP(anti-U1RNP +), CC (anti-Ro/SSA+), IK(anti-U1RNP +), JP(anti-dsDNA alone)], three samples of affinity-purified anti-dsDNA IgG from patient sera LG, Ap, and CC [anti-dsDNA(LG), anti-dsDNA(AP), and anti-dsDNA(CC), respectively], and 33.H11 IgG were used as anti-dsDNA-positive samples. As negative controls, two normal human sera (DB and CW), SLE patient FF serum containing only antibodies to U1RNP and Sm (anti-U1RNP/Sm), and SLE patient NK serum containing only antibodies to Ro/SSA and La/SSB (anti-Ro/La) were used. Three SLE patient sera (JC, AR, and MH) were used as anti-ribosomal protein P antibodies (anti-P) positive sera. Antibodies to U1RNP, Sm, Ro/SSA, La/SSB, or ribosomal protein P were detected by double immunodiffusion using bovine spleen or calf thymus extract (Clark, et al., *J. Immunol.* 102:117 (1969); Mattioli and Reichlin, *Arthritis Rheum.* 17:421 (1974)). Human Cohn fraction II (Sigma) was used for normal human IgG.

Inhibition of in vitro Translation

A procedure based on Targoff, et al., *J. Clin. Invest.* 84:162 (1989), was used, modified as follows. A standard translation reaction using a rabbit reticulocyte lysate system kit (Boehringer Mannheim Corp., Indianapolis, Ind.) with rabbit globin mRNA was set up, with [$^3$H]leucine (ICN) as the labeled amino acid. Then 10 µl of the rabbit reticulocyte lysate were preincubated with 1 unit of RQ1 DNase (RNase-free) (Promega) (or water alone as negative control) for 30 min at 37° C. Purified IgG was dialyzed against water and concentrated. Lysate with or without DNase treatment was preincubated with IgG solution (or water alone as negative control) which contains 1 unit of RNase inhibitor (Sigma) for 2 h at 4° C. After adding all the reaction components and 5 µl of rabbit globin mRNA (Life Technologies Inc., Gaithersburg, Md.), the lysate was incubated for 1 h at 30° C. to start translation (completing a 32.5-µl reaction volume). After incubating with 3.25 µl of 1 mg/ml RNase A for 15 min at 30° C., 5 µl of the reaction was spotted on glass fiber filters. After washes with 5% TCA and ethanol, cpm of the filters were determined by liquid scintillation counting. Translation reaction was determined as the average of duplicate translation runs (cpm). Fidelity of the replicates was assessed by calculating the Pearson correlation coefficient.

$$\frac{\% \text{ inhibition}}{100} = \frac{\text{cpm after no } IgG \text{ added} - \text{cpm after } IgG \text{ added}}{\text{cpm after no } IgG \text{ added}}$$

Results

RNA Immunoprecipitation by Anti-dsDNA Antibodies

The labeled cell extract was treated with DNase before RNA-IP was performed because it is possible that labeled DNAs, which are precipitated by anti-dsDNA antibodies, are detected on the non-denaturing polyacrylamide gel as background. DNase-treated $^{32}$P-labeled MOLT4 cell extract was incubated with Protein A Sepharose 4B-bound antibodies. Precipitated RNAs were analyzed on a 2.5% polyacrylamide non-denaturing gel: 33.H11 IgG (1.0 µg); anti-dsDNA-positive patient sera LG, CC, JP, IL, respectively; normal human serum DB; normal human IgG from Con fraction II (1.0 µg); affinity-purified anti-dsDNA IgG (1.0 µg each) from sera LG, AP, CC, respectively; serum NK containing only anti-Ro/La antibodies; serum FF containing only anti-U1RNP/Sm antibodies; JC and MH sera containing both anti-P and anti-dsDNA antibodies, respectively; serum AR containing only anti-P antibodies. 33.H11 (0.1 µg) was preincubated with 100 µg/ml each of Yeast tRNA, calf thymus dsDNA, BSA, or the recombinant ribosomal protein S1 (G7-RP). 33.H11 (0.1 µg) did not immunoprecipitate 18S RNA when deproteinized MOLT4 cell extract was used as the antigen. As shown in the Western blot, all four sera containing anti-dsDNA antibodies precipitated 18S RNA whereas normal human serum, serum containing only anti-Ro/La, or only anti-U1RNP/Sm antibodies did not. Moreover, 1.0 µg of 33.H11 and 1.0 µg each of affinity-purified anti-dsDNA IgG precipitated 18S RNA while 1.0 µg of normal IgG from Cohn fraction II did not. Two sera Containing both anti-P and anti-dsDNA antibodies precipitated 18S RNA whereas the serum containing only anti-P antibodies did not. Therefore, it was concluded that anti-dsDNA antibodies immunoprecipitate 18S ribosomal RNA specifically.

From the observation of RNA-IP using deproteinized MOLT4 cell extract as the source of antigen, the absence of 18S RNA precipitates by 0.1 µg of 33.H11 IgG indicates that proteins are essential for 18S RNA immunoprecipitation by anti-dsDNA antibodies. 1.0 µg of 33.H11 IgG did not precipitate 18S RNA, either, when deproteinized cell extract was used as the antigen.

A quantity (0.1 µg) of 33.H11, that reacts strongly with both G7-RP and calf thymus dsDNA, was preincubated with 100 µg/ml each of G7-RP, BSA, calf thymus dsDNA, or Yeast tRNA before RNA-IP was performed. As a result, 18S RNA immunoprecipitation by 33.H11 was inhibited completely by 100 µg/ml each of G7-RP and calf thymus dsDNA whereas it was not blocked by the same concentration of either BSA or tRNA. These results suggest that G7-RP is essential for 18S ribosomal RNA immunoprecipitation by anti-dsDNA antibodies.

TABLE II

Inhibition of in vitro translation by anti-dsDNA Antibodies

| Samples | | DNase treatment of reticulocyte lysate | | |
|---|---|---|---|---|
| | | (−) CPM (% INHIB) | (+) CPM (% INHIB) | Change |
| no added IgG [mRNA(−)] | | 2,243 (___) | 892 (___) | — |
| no added IgG [mRNA(+)] | | 60,777 (___) | 46,966 (___) | — |
| <whole serum IgG> | | | | |
| LG IgG (anti-dsDNA) | 9 μg | 48,261 (20.6) | 16,233 (65.4) | +44.8 |
| AP IgG (anti-dsDNA) | 9 μg | 56,796 ( 6.6) | 23,358 (50.3) | +43.7 |
| CC IgG (anti-dsDNA) | 9 μg | 83,765 ( 0) | 17,399 (63.1) | +63.1 |
| FF IgG (anti-U1RNP/Sm) | 9 μg | 72,558 ( 0) | 47,477 ( 0) | 0 |
| NK IgG (anti-Ro/La) | 9 μg | 79,896 ( 0) | 48,678 ( 0) | 0 |
| DB IgG (normal) | 9 μg | 91,999 ( 0) | 45,598 ( 2.9) | +2.9 |
| CW IgG (normal) | 9 μg | 83,749 ( 0) | 44,165 ( 6.0) | +6.0 |
| <affinity-purified IgG> | | | | |
| anti-dsDNA(LG) IgG | 1 μg | 37,105 (38.9) | 19,680 (58.1) | +19.2 |
| | 3 μg | 36,768 (39.5) | 15,520 (67.0) | +27.5 |
| anti-dsDNA(AP) IgG | 1 μg | 34,539 (43.2) | 12,864 (72.6) | +29.4 |
| | 3 μg | 35,555 (41.5) | 12,659 (73.0) | +31.5 |
| anti-dsDNA(CC) IgG | 1 μg | 50,590 (16.8) | 14,247 (69.7) | +52.9 |
| | 3 μg | 38,477 (36.7) | 13,946 (70.3) | +33.6 |
| 33.H11 IgG | 1 μg | 38,021 (37.4) | 11,853 (74.8) | +37.4 |
| | 3 μg | 30,076 (50.5) | 9,503 (79.8) | +29.3 |
| Normal human IgG | 1 μg | 74,470 ( 0) | 48,714 ( 0) | 0 |
| (Cohn fraction II) | 3 μg | 78,178 ( 0) | 49,692 ( 0) | 0 |

Each sample was tested after adding of 1, 3, or 9 μg of IgG. CPM, average of duplicate translation runs (cpm in a 5-μl reaction mixture). % INHIB, % inhibition defined in the text. Change, differences in % inhibition that resulted from the incubation with DNase-treated lysate as compared to the incubation with non-DNase-treated lysate.

Inhibition of in vitro Translation by Anti-dsDNA Antibodies

As shown in Table II, in vitro translation of rabbit globin mRNA was not affected by the addition of 9.0 μg of whole IgG from FF (anti-U1RNP/Sm), NK (anti-Ro/La), DB (normal), CW (normal) serum, or 1.0 and 3.0 μg or normal human IgG (Cohn fraction II) when either DNase-treated or non-treated reticulocyte lysate was used. The small inhibition (2.9–6.0%) noted with these negative control antibodies in the DNase-treated reticulocyte lysate was considered to be nonspecific inhibition. Nine μg of whole IgG from anti-dsDNA-positive LG, AP, or CC serum, which inhibited the translation poorly or not at all when the lysate was not treated with DNase, inhibited translation to a considerable degree (50–65%) when the lysate was treated with DNase. However, only 1.0 μg of affinity-purified anti-dsDNA IgG [anti-dsDNA(LG) and anti-dsDNA(AP)] or the monoclonal anti-dsDNA 33.H11 IgG were required for translation inhibition (38–43%) even if the lysate was not treated with DNase. Moreover, this translation inhibition by 1.0 μg of affinity-purified anti-dsDNA and 33.H11 IgG was uniformly and significantly enhanced when the reticulocyte lysate was treated with DNase (see Table II). As the degrees of translation inhibition by 1.0 or 3.0 μg of affinity-purified anti-dsDNA and 33.H11 IgG were very similar, the inhibitory effect of anti-dsDNA IgG was apparently maximal (67–80% when DNase-treated lysate was used) with 3.0 μg of affinity-purified anti-dsDNA IgG added. The quality of the duplicate samples was reflected by the calculated value of the Pearson correlation coefficient $r^2=0.972$ for the whole data set.

Discussion

In the study of RNA-IP, it was demonstrated that anti-dsDNA antibodies precipitated only 18S RNA whereas normal human IgG and other autoantibodies (antibodies to U1RNP, Sm, Ro/SSA, La/SSB, or ribosomal protein P) did not. Also, this 18S RNA immunoprecipitation was inhibited by preincubating 33.H11 with calf thymus dsDNA or with the recombinant r-protein S1 (G7-Rp). Thus, it was concluded that anti-dsDNA antibodies precipitate 18S ribosomal RNA specifically. Moreover, it was demonstrated that r-protein S1 is essential for 18S RNA immunoprecipitation by anti-dsDNA antibodies. These results might support the evidence that r-protein S1 is located on the 40S ribosomal subunit (in eukaryotes) where 18S ribosomal RNA is an integral component. In Example 1, it was shown that the differences of the staining pattern by anti-dsDNA antibodies in IF (classical nuclear pattern versus nucleolar and cytoplasmic pattern represented by 33.H11) are due to the differences of anti-dsDNA Ab affinity between r-protein S1 and dsDNA. In the study described above, 33.H11, which has a higher affinity for r-protein S1 than for dsDNA, penetrate the plasma membrane, localizes in the cytoplasm, and remains there even after 48 hours of observation. From these standpoints, the observation of RNA-IP in this study suggests not only that the anti-dsDNA antibodies which have higher affinity for dsDNA can recognize r-protein S1 but also the possibility that anti-dsDNA antibodies recognize r-protein S1 in the cytoplasm after penetrating cell membranes. Furthermore, as RNA-IP is one of the methods for detecting antibodies to native RNA-related proteins, the results as described above indicate that anti-dsDNA antibodies can recognize the native form of human r-protein S1.

The r-protein S1 in *E.coli* is well known to be associated with the 30S ribosomal subunit via its N-terminal globular domain. It has been reported that the major function of r-protein S1 of *E.coli* in protein synthesis is at the mRNA binding step, as described by Subramanian, *Prog. Nucleic Acids Res. Mol. Biol.* 28:101 (1983). Thus this protein plays a key role in translation initiation of *E.coli*. The translation inhibition of globin mRNA by anti-dsDNA antibodies was then determined. There are to our knowledge no published studies describing a role for r-protein S1 or its analogue in eukaryotic cells but these experiments suggest such a role. However, some anti-dsDNA antibodies might have much higher affinity for dsDNA than for r-protein S1. Therefore, the rabbit reticulocyte lysate was treated with DNase to investigate more sensitively the translation inhibition. The conclusion from these data is that anti-dsDNA antibodies inhibit the translation of globin mRNA even when some dsDNA exist in the reticulocyte lysate and that the inhibition is greatly enhanced when free dsDNA is eliminated by DNase treatment.

It is possible that anti-dsDNA antibodies inhibit the translation of mRNA by recognizing the mRNA binding sites on the eukaryotic analogue of r-protein S1 and by inhibiting the mRNA binding to r-protein S1. Demonstration of a powerful inhibition of protein synthesis by anti-dsDNA antibodies by its interaction with the human r-protein S1 provides a mechanism for a pathogenic role of anti-dsDNA antibodies after their penetration of living cells.

EXAMPLE 3

Demonstration of Broad Cross-reactivity of an Anti-Id Reagent with Anti-dsDNA from SLE Patients Normal human serum was used as the source of the anti-Id that was prepared by passage of normal human serum over a column made with affinity purified anti-dsDNA Fab from a single lupus patient. Elution of the anti-Id with 3 M $MgCl_2$ and pepsin digestion resulted in anti-Id $Fab_2$ which was used to coat immulon plates. Five different affinity purified polyclonal anti-dsDNA populations were then shown to bind the anti-Id $Fab_2$ much more strongly than to normal Cohn fraction FII $Fab_2$, about two-fold on average. In addition two human monoclonal IgG anti-dsDNA antibody samples bound the anti-Id $Fab_2$ more strongly than control CFII $Fab_2$. In all cases dsDNA, but not RNA, blocked the interactions between the anti-Id $Fab_2$ and the various anti-dsDNA preparations. Affinity purified anti-Ro/SSA, anti-La/SSB, anti-U1RNP and normal CFII IgG preparations bound anti-Id $Fab_2$ and control CFII $Fab_2$ equally. This broad and specific cross-reactivity of anti-dsDNA from different SLE patients and an anti-Id (anti-anti-Id dsDNA) from a normal person has not been previously recognized and has potential as an immunologically specific reagent to block and/or downregulate anti-dsDNA in SLE.

Modifications and variations of the present invention will be obvious to those skilled in the art intended to come within the scope of the claims.

We claim:

1. A method for treating a lupus patient having anti-dsDNA antibodies comprising administering to the patient a therapeutic composition in a pharmaceutically acceptable carrier for administration to a patient selected from the group consisting of peptides between four and forty amino acids in length which have sequence identity with ribosomal protein SI and which are immunoreactive with anti-dsDNA antibodies, and anti-idiotypic monoclonal antibody or antibody fragments immunoreactive with anti-dsDNA antibodies which are cross-reactive with human ribosomal protein S1 and which bind with greater affinity to ribosomal protein S1.

2. The method of claim 1 wherein the peptide is conjugated to a carrier molecule or is a fusion protein.

3. The method of claim 1 wherein the composition is a peptide administered to a patient in an amount effective to induce tolerance.

4. The method of claim 1 wherein the composition is anti-idiotypic monoclonal antibody immunoreactive with anti-dsDNA which are cross-reactive with human ribosomal protein S1 and which bind with greater affinity to ribosomal protein S1.

5. The method of claim 4 wherein the anti-idiotypic antibody immunoreactive with anti-dsDNA antibody is administered in a dosage effective to kill anti-dsDNA antibody producing cells.

6. The method of claim 4 wherein the antibody is administered in a dosage effective to decrease the amount of anti-dsDNA antibody levels in the patient.

7. A therapeutic composition in a pharmaceutically acceptable carrier for administration to a patient selected from the group consisting of peptides between four and forty amino acids in length which have sequence identity with ribosomal protein S1 and which are immunoreactive with anti-dsDNA and anti-idiotypic monoclonal antibody or antibody fragments immunoreactive with anti-dsDNA antibodies which are cross-reactive with human ribosomal protein S1 and which bind with greater affinity to ribosomal protein S1.

8. The composition of claim 7 wherein the peptide is conjugated to a carrier molecule or is a fusion protein.

9. The composition of claim 7 wherein the composition is a peptide formulated in a dosage for administration to a patient in an amount effective to induce tolerance.

10. The composition of claim 7 wherein the composition is anti-idiotypic monoclonal antibody immunoreactive with anti-dsDNA antibody which are cross-reactive with human ribosomal protein S1 and which bind with greater affinity to ribosomal protein S1.

11. The composition of claim 10 wherein the antibody is formulated in a dosage effective to kill anti-dsDNA antibody producing cells.

12. The composition of claim 10 wherein the antibody is formulated in a dosage effective to decrease the amount of anti-dsDNA antibody levels in the patient.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1314 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:1:

```
GGTGAAGAAG GAGTTGTGCC AGCACGTGAG TACTCAGACG ATCGTAACAT CAACCTGGCA      60

GACGAATTAA AAATTGGTGA TACCATTGAA GCAGTTGTCA TTTCTAACGT AACAAGCGAC     120

AAGGAAGGCG TCAGTTACTT GTTGTCAAAG AAGCGTTTGG ATGCGCGCAA GGCATGGGAA     180

AACTTGAGCT TTGCTGAAGG TGACACAGTT GATGCCAAGG TTATCAACGC TGTTCGTGGT     240

GGTTTGATTG TTGATGTTAA CGGCGTACGT GGTTTCGTAC CAGCATCAAT GGTTGCAGAA     300

CGTTTCGTTT CTGATTTGAA CCAATTCAAG AATAAGGATA TTAAAGCACA AGTTATCGAA     360
```

```
ATTGACCCTG CTAATGCACG TTTGATTTTG TCACGTAAGG CTGTTGCTGC ACAAGAACGC    420

GCTGCACGAT TGGCTGAAGT ATTTAGCAAG TTGTCAGTTC GTGAAGTTGT TGAAGGAACT    480

GTTGCCCGTT TGACAGACTT CGGCGCATTC GTTGACTTGG GTGGTGTTGA TGGTTTGGTT    540

CACGTATCAG AAATCTCACA CGATCGTGTG AAGAACCCGG CCGATGTATT GACAAAGGGT    600

GACAAGGTTG ATGTTAAGAT CTTGGCATTG GACACTGAAA AGGGTCGTAT CTCATTGTCA    660

ATCAAAGCAA CACAACGTGG ACCTTGGGAC GAAGCTGCAG ATCAAATCGC TGCAGGTTCA    720

GTGCTTGAAG GTACTGTTAA GCGTGTGAAG GACTTTGGTG CCTTTGTTGA AATTTTGCCT    780

GGTATCGAAG GTCTTGTGCA CGTGTCACAA ATTTCAAACA AGCGTATTGA AAACCCATCA    840

GAAGTTTTGA AGTCTGGTGA CAAGGTACAA GTGAAGGTAT TGGACATTAA GCCAGCCGAA    900

GAACGTATTT CATTGTCAAT GAAGGCTTTG GAAGAAAAGC CAGAACGTGA AGATCGTCGT    960

GGTAACGATG GTTCAGCTTC ACGTGCTGAT ATCGCTGCTT ACAAGCAACA AGATGACTCA   1020

GCCGCAACAT TGGGTGACAT CTTTGGTGAT AAGTTGTAAG AGGCATCAAC ATAAAAGAGC   1080

TGGTTCGCCA GTTCTTTTAT TTTTGAAGAA AAATTGAGTG GGCATTAGTG GGCGCTCACG   1140

GTATGAAAAA GGAGGTGCGA TTATGGCAGC ACCAGTAGTA GCCATTGTTG GCGACCAAAC   1200

GTCGGAAAAT CGACTATCTT TAACCGGATG GCCGGAGAAC GTATTGCAAT TGTTGAAGAT   1260

CAACCAGGGG TAACACGCGA TCGTTTGTAC GCGCCAGCCG AATGGTTGAA TTAT         1314
```

(2) INFORMATION FOR SEQ ID NO:2:

(i) SEQUENCE CHARACTERISTICS:
        (A) LENGTH: 352 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:2:

```
Gly Glu Glu Gly Val Val Pro Ala Arg Glu Tyr Ser Asp Asp Arg Asn
1               5                   10                  15

Ile Asn Leu Ala Asp Glu Leu Lys Ile Gly Asp Thr Ile Glu Ala Val
            20                  25                  30

Val Ile Ser Asn Val Thr Ser Asp Lys Glu Gly Val Ser Tyr Leu Leu
        35                  40                  45

Ser Lys Lys Arg Leu Asp Ala Arg Lys Ala Trp Glu Asn Leu Ser Phe
    50                  55                  60

Ala Glu Gly Asp Thr Val Asp Ala Lys Val Ile Asn Ala Val Arg Gly
65                  70                  75                  80

Gly Leu Ile Val Asp Val Asn Gly Val Arg Gly Phe Val Pro Ala Ser
                85                  90                  95

Met Val Ala Glu Arg Phe Val Ser Asp Leu Asn Gln Phe Lys Asn Lys
            100                 105                 110

Asp Ile Lys Ala Gln Val Ile Glu Ile Asp Pro Ala Asn Ala Arg Leu
        115                 120                 125

Ile Leu Ser Arg Lys Ala Val Ala Ala Gln Glu Arg Ala Ala Gln Leu
    130                 135                 140

Ala Glu Val Phe Ser Lys Leu Ser Val Gly Glu Val Val Glu Gly Thr
145                 150                 155                 160
```

```
Val Ala Arg Leu Thr Asp Phe Gly Ala Phe Val Asp Leu Gly Gly Val
                165                 170                 175

Asp Gly Leu Val His Val Ser Glu Ile Ser His Asp Arg Val Lys Asn
            180                 185                 190

Pro Ala Asp Val Leu Thr Lys Gly Asp Lys Val Asp Val Lys Ile Leu
            195                 200                 205

Ala Leu Asp Thr Glu Lys Gly Arg Ile Ser Leu Ser Ile Lys Ala Thr
            210                 215                 220

Gln Arg Gly Pro Trp Asp Glu Ala Ala Asp Gln Ile Ala Ala Gly Ser
225                 230                 235                 240

Val Leu Glu Gly Thr Val Lys Arg Val Lys Asp Phe Gly Ala Phe Val
                245                 250                 255

Glu Ile Leu Pro Gly Ile Glu Gly Leu Val His Val Ser Gln Ile Ser
                260                 265                 270

Asn Lys Arg Ile Glu Asn Pro Ser Glu Val Leu Lys Ser Gly Asp Lys
                275                 280                 285

Val Gln Val Lys Val Leu Asp Ile Lys Pro Ala Glu Glu Arg Ile Ser
            290                 295                 300

Leu Ser Met Lys Ala Leu Glu Glu Lys Pro Glu Arg Glu Asp Arg Arg
305                 310                 315                 320

Gly Asn Asp Gly Ser Ala Ser Arg Ala Asp Ile Ala Ala Tyr Lys Gln
                325                 330                 335

Gln Asp Asp Ser Ala Ala Thr Leu Gly Asp Ile Phe Gly Asp Lys Leu
                340                 345                 350

(2) INFORMATION FOR SEQ ID NO:3:

(i) SEQUENCE CHARACTERISTICS:
        (A) LENGTH: 255 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:3:

Ser Phe Ala Glu Gly Asp Thr Val Asp Ala Lys Val Ile Asn Ala Val
1               5                   10                  15

Arg Gly Gly Leu Ile Val Asp Val Asn Gly Val Arg Gly Phe Val Pro
                20                  25                  30

Ala Ser Met Val Ala Glu Arg Phe Val Ser Asp Leu Asn Gln Phe Lys
                35                  40                  45

Asn Lys Asp Ile Lys Ala Gln Val Ile Glu Ile Asp Pro Ala Asn Ala
            50                  55                  60

Arg Leu Ile Leu Ser Arg Lys Ala Val Ala Gln Glu Arg Ala Ala
65                  70                  75                  80

Gln Leu Ala Glu Val Phe Ser Lys Leu Ser Val Gly Glu Val Val Glu
                85                  90                  95

Gly Thr Val Ala Arg Leu Thr Asp Phe Gly Ala Phe Val Asp Leu Gly
                100                 105                 110

Gly Val Asp Gly Leu Val His Val Ser Glu Ile Ser His Asp Arg Val
            115                 120                 125

Lys Asn Pro Ala Asp Val Leu Thr Lys Gly Asp Lys Val Asp Val Lys
```

-continued

```
            130                 135                 140
Ile Leu Ala Leu Asp Thr Glu Lys Gly Arg Ile Ser Leu Ser Ile Lys
145                 150                 155                 160

Ala Thr Gln Arg Gly Pro Trp Asp Glu Ala Ala Asp Gln Ile Ala Ala
                165                 170                 175

Gly Ser Val Leu Glu Gly Thr Val Lys Arg Val Lys Asp Phe Gly Ala
                180                 185                 190

Phe Val Glu Ile Leu Pro Gly Ile Glu Gly Leu Val His Val Ser Gln
                195                 200                 205

Ile Ser Asn Lys Arg Ile Glu Asn Pro Ser Glu Val Leu Lys Ser Gly
                210                 215                 220

Asp Lys Val Gln Val Lys Val Leu Asp Ile Lys Pro Ala Glu Glu Arg
225                 230                 235                 240

Ile Ser Leu Ser Met Lys Ala Leu Glu Glu Lys Pro Glu Arg Glu
                245                 250                 255
```

(2) INFORMATION FOR SEQ ID NO:4:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:4:

```
Ala Tyr Glu Asp Ala Glu Thr Val Thr Gly Val Ile Asn Gly Lys Val
1                   5                   10                  15

Lys Gly Gly Phe Thr Val Glu Leu Asp Gly Ile Arg Ala Phe Leu Pro
                20                  25                  30

Gly Ser Leu Val Asp Val Arg Pro Val Arg Asp Thr Leu His Leu Glu
                35                  40                  45

Gly Lys Glu Leu Glu Phe Lys Val Ile Lys Leu Asp Gln Lys Arg Asn
                50                  55                  60

Asn Val Val Ser Arg Arg Ala Val Ile Glu Ser Glu Asn Ser Ala
65                  70                  75                  80

Glu Arg Asp Gln Leu Leu Glu Asn Leu Gln Glu Gly Met Glu Val Lys
                85                  90                  95

Gly Ile Val Lys Asn Leu Thr Asp Tyr Gly Ala Phe Val Asp Leu Gly
                100                 105                 110

Gly Val Asp Gly Leu Leu His Ile Thr Asp Met Ala Trp Lys Arg Val
                115                 120                 125

Lys His Pro Ser Glu Ile Val Asn Val Gly Asp Glu Ile Thr Val Lys
                130                 135                 140

Val Leu Lys Phe Asp Arg Glu Arg Thr Arg Val Ser Leu Gly Leu Lys
145                 150                 155                 160

Gln Leu Gly Glu Asp Pro Trp Val Ala Ile Ala Lys Arg Tyr Pro Glu
                165                 170                 175

Gly Thr Lys Leu Thr Gly Arg Val Thr Asn Leu Thr Asp Tyr Gly Cys
                180                 185                 190

Phe Val Glu Ile Glu Glu Gly Val Glu Gly Leu Val His Val Ser Glu
                195                 200                 205
```

```
Met Arg Asp Arg Val Glu Asp Ala Thr Leu Val Leu Ser Val Gly Asp
    210                 215                 220
Glu Val Glu Ala Lys Phe Thr Gly Val Asp Arg Lys Asn Arg Ala Ile
225                 230                 235                 240
Ser Leu Ser Val Arg Ala Lys Asp Glu Ala Asp Glu Lys Asp
                245                 250
```

(2) INFORMATION FOR SEQ ID NO:5:

(i) SEQUENCE CHARACTERISTICS:
        (A) LENGTH: 247 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:5:

```
Lys Phe Glu Ala Gly Glu Arg Val Glu Gly Ile Ile Phe Asn Gln Val
1               5                   10                  15
Lys Gly Gly Phe Thr Val Asp Leu Asp Gly Ala Val Ala Phe Leu Pro
                20                  25                  30
Arg Ser Gln Val Asp Ile Arg Pro Ile Arg Asp Val Thr Pro Ala Asp
            35                  40                  45
Ala Gln Pro Ala Ala Leu Arg Asn Leu Lys Met Asp Lys Arg Arg Gly
        50                  55                  60
Asn Ile Val Val Ser Arg Arg Thr Val Leu Glu Glu Ser Arg Ala Glu
65                  70                  75                  80
Gln Arg Ser Glu Ile Val Gln Asn Leu Glu Glu Gly Gln Val Val Glu
                85                  90                  95
Gly Val Val Lys Asn Ile Thr Asp Tyr Gly Ala Phe Val Asp Leu Gly
                100                 105                 110
Gly Ile Asp Gly Leu Leu His Val Thr Asp Met Ala Trp Arg Arg Val
            115                 120                 125
Lys His Pro Ser Glu Ile Gln Asn Ile Gly Gln Gln Val Lys Val Gln
        130                 135                 140
Ile Ile Arg Ile Asn Gln Glu Thr His Arg Ile Ser Leu Gly Met Lys
145                 150                 155                 160
Gln Leu Glu Ser Asp Pro Trp Asp Gly Ile Gly Ala Lys Tyr Pro Val
                165                 170                 175
Gly Lys Lys Ile Ser Gly Thr Val Thr Asn Ile Thr Asp Tyr Gly Ala
                180                 185                 190
Phe Val Glu Leu Glu Pro Gly Ile Glu Gly Leu Ile His Ile Ser Glu
            195                 200                 205
Met Asn Arg Pro Gly Glu Gln Val Ile Glu Glu Phe Asn Lys Gly Asp
        210                 215                 220
Val Val Arg Ala Val Val Leu Asp Val Asp Val Asp Lys Glu Arg Ile
225                 230                 235                 240
Ser Leu Gly Ile Lys Gln Leu
                245
```

(2) INFORMATION FOR SEQ ID NO:6:

(i) SEQUENCE CHARACTERISTICS:
        (A) LENGTH: 235 amino acids

```
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:6:

Glu Thr Val Thr Gly Val Ile Asn Gly Lys Val Lys Gly Gly Phe Thr
1               5                   10                  15

Val Glu Leu Asn Gly Ile Arg Ala Phe Leu Pro Gly Ser Leu Val Asp
            20                  25                  30

Val Arg Pro Val Arg Asp Thr Thr His Leu Glu Gly Lys Glu Leu Glu
        35                  40                  45

Phe Lys Val Ile Lys Leu Asp Gln Lys Arg Asn Asn Val Val Val Ser
    50                  55                  60

Arg Arg Ala Val Ile Glu Ser Glu Ser Ser Ala Glu Arg Asp Gln Leu
65                  70                  75                  80

Leu Glu Asn Leu Gln Glu Gly Met Glu Val Lys Gly Ile Val Lys Asn
                85                  90                  95

Leu Thr Asp Tyr Gly Ala Phe Val Asp Leu Gly Gly Val Asp Gly Leu
            100                 105                 110

Leu His Ile Thr Asp Met Ala Trp Lys Arg Val Lys His Pro Ser Glu
        115                 120                 125

Ile Val Asn Val Gly Asp Glu Ile Thr Val Lys Val Leu Lys Phe Asp
    130                 135                 140

Arg Glu Arg Thr Arg Val Ser Leu Gly Leu Lys Gln Leu Gly Glu Asp
145                 150                 155                 160

Pro Trp Val Ala Ile Ala Lys Arg Tyr Pro Glu Gly Thr Lys Leu Thr
                165                 170                 175

Gly Arg Val Thr Asn Leu Thr Asp Tyr Gly Cys Phe Val Glu Ile Glu
            180                 185                 190

Glu Gly Val Glu Gly Leu Val His Val Ser Glu Met Lys Lys Gly Asp
        195                 200                 205

Glu Ile Ala Ala Val Val Leu Gln Val Asp Ala Glu Arg Glu Arg Ile
    210                 215                 220

Ser Leu Gly Val Lys Gln Leu Ala Glu Asp Pro
225                 230                 235

(2) INFORMATION FOR SEQ ID NO:7:

(i) SEQUENCE CHARACTERISTICS:
            (A) LENGTH: 162 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:7:

Ala Glu Asp Val Val Val Lys Gly Lys Ile Val Gly Ala Asn Lys Gly
1               5                   10                  15

Gly Val Val Ala Leu Val Glu Gly Leu Arg Gly Phe Val Pro Phe Ser
            20                  25                  30
```

```
Gln Ile Ser Ser Lys Ser Ala Glu Glu Leu Leu Glu Lys Glu Ile
         35                  40                  45

Pro Leu Lys Phe Val Glu Val Asp Glu Glu Gln Ser Arg Leu Val Met
 50                  55                  60

Ser Asn Arg Lys Ala Met Ala Asp Ser Gln Ala Met Ala Asp Ser Gln
 65                  70                  75                  80

Ala Gln Leu Gly Ile Gly Ser Val Val Thr Gly Thr Val Gln Ser Leu
                     85                  90                  95

Lys Pro Tyr Gly Ala Phe Ile Asp Ile Gly Ile Asn Gly Leu Leu
                100                 105                 110

His Val Ser Gln Ile Ser His Asp Arg Val Ser Asp Ile Ala Thr Val
            115                 120                 125

Leu Gln Pro Gly Asp Thr Leu Lys Val Met Ile Leu Ser His Asp Arg
130                 135                 140

Glu Arg Gly Arg Val Ser Leu Ser Thr Lys Lys Leu Glu Pro Thr Pro
145                 150                 155                 160

Gly Asp
```

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:8:

```
Glu Gly Thr Val
 1
```

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:9:

```
Asp Phe Gly Ala Phe Val
 1               5
```

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO -continued (iv) ANTI-SENSE: NO (xi) SEQUENCE DESCRIPTION: SEQ ID NO:10:

Gly Leu Val His Val Ser
1               5

(2) INFORMATION FOR SEQ ID NO:11:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:11:

Gly Asp Lys Val
1

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:12:

Arg Ile Ser Leu Ser
1               5